(12) United States Patent
Yonemitsu et al.

(10) Patent No.: US 7,314,614 B1
(45) Date of Patent: *Jan. 1, 2008

(54) RECOMBINANT SENDAI VIRUS VECTOR FOR INTRODUCING EXOGENOUS GENES TO AIRWAY EPITHELIA

(75) Inventors: Yoshikazu Yonemitsu, Fukuoka (JP); Mamoru Hasegawa, Ibaraki (JP); Eric W F W Alton, London (GB)

(73) Assignee: DNAVEC Research, Inc., Ibaraki (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/111,356

(22) PCT Filed: Nov. 2, 2000

(86) PCT No.: PCT/JP00/07737

§ 371 (c)(1),
(2), (4) Date: Jul. 30, 2002

(87) PCT Pub. No.: WO01/32898

PCT Pub. Date: May 10, 2001

Related U.S. Application Data

(60) Provisional application No. 60/163,055, filed on Nov. 2, 1999.

(30) Foreign Application Priority Data

Dec. 17, 1999 (JP) ................... 11-359218

(51) Int. Cl.
| | |
|---|---|
| *A01N 63/00* | (2006.01) |
| *A01N 65/00* | (2006.01) |
| *A01N 43/04* | (2006.01) |
| *A01K 31/70* | (2006.01) |
| *C12N 15/00* | (2006.01) |
| *C12N 5/00* | (2006.01) |
| *C12N 5/02* | (2006.01) |

(52) U.S. Cl. .................. 424/93.1; 514/44; 435/325; 435/320.1

(58) Field of Classification Search ............ 536/23.1, 536/23.5; 514/44; 424/93.1; 435/455; 800/21
See application file for complete search history.

(56) References Cited

U.S. PATENT DOCUMENTS

| | | | |
|---|---|---|---|
| 5,670,488 A * | 9/1997 | Gregory et al. ............ 514/44 |
| 5,824,655 A * | 10/1998 | Border ..................... 514/44 |
| 5,958,893 A * | 9/1999 | Welsh et al. ............... 514/44 |
| 6,645,760 B2 | 11/2003 | Nagai et al. |
| 6,723,532 B2 * | 4/2004 | Nagai et al. ................ 800/8 |
| 6,746,860 B1 | 6/2004 | Tokusumi et al. |
| 6,828,138 B1 | 12/2004 | Nagai et al. |
| 2002/0002143 A1 | 1/2002 | Kano et al. |
| 2002/0098576 A1 * | 7/2002 | Nagai et al. ............. 435/320.1 |
| 2002/0100066 A1 * | 7/2002 | Nagai et al. ................ 800/8 |
| 2003/0166252 A1 | 9/2003 | Kitazato et al. |
| 2003/0170210 A1 | 9/2003 | Masaki et al. |
| 2003/0170266 A1 | 9/2003 | Kitazato et al. |
| 2003/0170897 A1 | 9/2003 | Imai et al. |
| 2003/0203489 A1 | 10/2003 | Yonemitsu et al. |
| 2004/0005296 A1 | 1/2004 | Yonemitsu et al. |
| 2004/0053877 A1 | 3/2004 | Fukumura et al. |
| 2004/0101965 A1 | 5/2004 | Griesenbach et al. |
| 2004/0121308 A1 | 6/2004 | Nagai et al. |
| 2006/0104950 A1 | 5/2006 | Okano et al. |
| 2007/0105208 A1 | 5/2007 | You et al. |

FOREIGN PATENT DOCUMENTS

| | | |
|---|---|---|
| EP | 0 863 202 A1 | 9/1998 |
| EP | 0 864 645 A1 | 9/1998 |

OTHER PUBLICATIONS

Deonarain (1998) Exp. Opin. Ther. Pat., 8(1): 53-69.*
Gorecki (2001) Exp. Opin. Emerging Drugs, 6(2): 187-98.*
Verma, et al. (1997) Nature, 389: 239-42.*
Eck, et al. (1996) Goodman & Gilman's The Pharmacological Basis of Therapeutics, 9th Ed., McGraw-Hill, New York, NY., pp. 77-101.*
Lamb, et al. (2001) Fundamental Virology, 4th Ed., Lippincott, Williams & Wilkins, New York, NY., p. 691.*
Jenkins, et al. (2003) Monaldi Arch. Chest Dis., 53: 17-24.*
Griesenbach, et al. (2003) Curr. Opin. Molec. Therap., 5(5) 489-94.*
Dzau, et al. (1996) Proc. Natl. Acad. Sci., USA, 93: 11421-25.*
Tashiro, et al. (1997) Frontiers in Bioscience 2: d588-91, internet publication, pp. 1-8.*
Kato, et al. (1997) J. Virol., 71(10): 7266-72.*
Hasan et al., "Creation of an Infectious Recombinant Sendai Virus Expressing the Firefly Luciferase Gene from the 3' Proximal First Locus," *Journal of General Virology* 78:2813-2820 (1997).
Saeki et al., "Development and Characterization of Cationic Liposomes Conjugated with HVJ (Sendai Virus): Reciprocal Effect of Cationic Lipid for in vitro and in vivo Gene Transfer," *Human Gene Therapy* 8:2133-2141 (1997).
Sakai et al., "Accommodation of Foreign Genes into the Sendai Virus Genome: Sizes of Inserted Genes and Viral Replication," *FEBS Letters* 456:221-226 (1999).
Yonemitsu et al., "HVJ (Sendai Virus)-Cationic Liposomes: A Novel and Potentially Effective Liposome-Mediated Technique for Gene Transfer to the Airway Epithelium," *Gene Therapy* 4:631-638 (1997).
Yonemitsu et al., "Efficient Gene Transfer to Airway Epithelium Using Recombinant Sendai Virus," *Nature Biotechnology* 18:970-973 (2000).

(Continued)

*Primary Examiner*—Joseph Woitach
*Assistant Examiner*—Robert M. Kelly
(74) *Attorney, Agent, or Firm*—Clark & Elbing LLP

(57) ABSTRACT

Provided are a recombinant Sendai virus vector for introducing exogenous genes to airway epithelia and a method for introducing exogenous genes using the vector. The recombinant Sendai virus vector enables efficient gene transfer to native mucus-layered airway epithelial cells by briefly contacting the vector with the cells. Furthermore, the vector can introduce genes to not only apical surfaces but also submucosal glands where CFTR primarily expresses. The vector can thus be used for gene therapy of CF, a CFTR-deficient disease.

17 Claims, 17 Drawing Sheets

OTHER PUBLICATIONS

McMorran et al., "G551D CF Mice Display an Abnormal Host Response and Have Impaired Clearance of *Pseudomonas* Lung Disease," Am. J. Physiol. Lung Cell Mol. Physiol. 281:L740-L747, (2001).

Cannon et al., "*Pseudomonas aeruginosa*-induced Apoptosis Is Defective in Respiratory Epithelial Cells Expressing Mutant Cystic Fibrosis Transmembrane Conductance Regulator," *Am. J. Respir. Cell Mol. Biol.* 29(2):188-197 (2003).

Delaney et al., "Cystic Fibrosis Mice Carrying the Missense Mutation G551D Replicate Human Genotype-Phenotype Correlations," *The EMBO Journal* 15(5):955-963 (1996).

Oceandy et al., "Gene Complementation of Airway Epithelium in the Cystic Fibrosis Mouse is Necessary and Sufficient to Correct the Pathogen Clearance and Inflammatory Abnormalities," *Human Molecular Genetics* 11(9):1059-1067 (2002).

Stonebraker et al., "Glycocalyx Restricts Adenoviral Vector Access to Apical Receptors Expressed on Respiratory Epithelium In Vitro and In Vivo: Role for Tethered Mucins as Barriers to Lumenal Infection," *Journal of Virology* 78(24):13755-13768 (2004).

Thomas et al., "G551D Cystic Fibrosis Mice Exhibit Abnormal Regulation of Inflammation In Lungs and Macrophages," *The Journal of Immunology* 164(7):3870-3877 (2000).

U.S. Appl. No. 10/543,734, filed Feb. 7, 2006, Tokusumi et al.

U.S. Appl. No. 10/562,408, filed Dec. 23, 2005, You et al.

Kato et al., "The paramyxovirus, Sendai virus, V protein encodes a luxury function required for viral pathogenesis," *EMBO J.* 16(3): 578-587, (1996).

* cited by examiner

A

B

RECOMBINANT SENDAI VIRUS VECTOR FOR INTRODUCING EXOGENOUS GENES TO AIRWAY EPITHELIA

This application claims priority from international application serial number PCT/JP00/07737, filed on Nov. 2, 2000, which in turn claims priority from Japanese application serial number JP 11-359218, filed on Dec. 17, 1999, and U.S. provisional application Ser. No. 60/163,055, filed on Nov. 2, 1999, the disclosures of which are hereby incorporated by reference.

TECHNICAL FIELD

The present invention relates to a recombinant Sendai virus vector for introducing exogenous genes to airway epithelia and a method for introducing exogenous genes using the vector.

BACKGROUND ART

With the advent of molecular cloning techniques, an expanding array of genes with mutations responsible for important human diseases have been identified and isolated. Absent or mutated genes in human patients can be replaced by ex vivo techniques, which include transformation of cells in vitro with naked DNA, DNA encapsulated in liposomes, appropriate integration vectors followed by introduction into a host organ ("ex vivo" gene therapy).

Gene therapy provides a means for transfer of a desired gene into a subject with the subsequent in vivo expression thereof. Gene transfer can be accomplished by transfecting the subject's cells or tissues ex vivo and reintroducing the transformed material into the host. Alternatively, genes can be administered directly to the recipient.

Nabel et al., Science (1990) 249: 1285-1288, pertains to in vivo intra-arterial transfection of pigs with liposomes containing a β-gal expression plasmid. Site-specific gene expression was observed in the arterial wall. There are several drawbacks to ex vivo therapy. For example, if only differentiated, replicating cells are infected, the newly introduced gene function will be lost as those cells mature and die. Ex vivo approaches also can be used to transfect only a limited number of cells and cannot be used to transfect cells which are not first removed from the body.

As described above, in gene therapy, it is very important to appropriately select a gene to be introduced, target cells in which the introduced gene is to be expressed, gene transfer methods suitable for target tissues, and the administration route.

Cystic fibrosis (CF) is an autosomal recessive genetic disease causing inborn error of metabolism. CF patients are frequently found in the U.S. and Europe, and one in every 2,000 to 2,500 infants suffers from this disease. As a major symptom, abnormal external secretion produces viscous secreta, which are accumulated in organs such as lung, respiratory tracts, pancreas, liver, and small intestine. The current therapy of CF focuses on lung transplantation and antibiotic treatment of pulmonary infectious diseases, which is particularly fatal.

The causative gene of CF, cystic fibrosis transmembrane conductance regulator (CFTR) gene, has been identified (Riordan, J. R. et al., Science 245: 1066-1073, 1989), and it is expected to develop gene therapy for CF in which a vector carrying a normal CFTR gene is introduced to airway epithelia. In gene therapy for CF, the exogenous gene should be introduced in vivo because ex vivo treatment cannot be applied to lung and upper airway.

Several attempts have been made to administer vectors to lung. Hazinski et al. (Am. J. Respir. Cell Mol. Biol. (1991) 4: 206-209) discloses liposome-mediated gene transfer of DNA into the intact rodent lung. Cationic liposomes were complexed to three fusion gene constructs composed of 1) the chloramphenicol acetyltransferase (CAT) gene linked to a Rous sarcoma virus (RSV) promoter; 2) the CAT gene linked to a mouse mammary tumor virus (MMTV) promoter; and 3) a cytomegalovirus-β-galactosidase (CMV-β-gal) fusion gene. The liposome/DNA complexes were instilled into the cervical trachea of rats and detectable levels of gene expression observed.

Brigham et al. (Am. J. Med. Sci. (1989) 298: 278-281) describes the in vivo transfection of murine lungs with the CAT gene using a liposome vehicle. Transfection was accomplished by intravenous, intratracheal or intraperitoneal injection. Both intravenous and intratracheal administration resulted in the expression of the CAT gene in the lungs. However, intraperitoneal administration did not.

Canonico et al. (Clin. Res. (1991) 39: 219A) describes the expression of the human α-1 antitrypsin gene, driven by the CMV promoter, in cultured bovine lung epithelial cells. The gene was added to cells in culture using cationic liposomes. The experimenters also detected the presence of α-1 antitrypsin in histological sections of the lung of New Zealand white rabbits following the intravenous delivery of gene constructs complexed to liposomes.

Furthermore, U.S. Pat. No. 5,958,893 discloses a method for introducing a gene encoding truncated CFTR using currently available vectors such as adenovirus vectors or cationic liposomes.

It was demonstrated, however, that adenovirus-mediated gene transfer to airway epithelia produced low gene transfer efficiency; low rate of uptake of adenoviral particles to the apical plasma membrane could be a cause of inefficient gene transfer, and lack of both the αβγ3 integrins and the CAR receptors which are the receptors for adenovirus, in apical surface of airway epithelial cells (Goldman, M. et al., Gene Ther. 3:811-818, 1996, Boucher, R. C., J. Clin. Invest 103: 441-445, 1999). In the case of cationic liposomes, mucus reportedly prevented their uptake, and gene transfer efficiency was improved by removal of the mucus (Kitson, C. et al., Gene Ther. 6: 534-546, 1999, Zabner, J. et al., J. Biol. Chem. 270: 18997-19007, 1995, Fasbender, A. et al., Gene Ther. 4: 1173-1180, 1997).

To date, no report is available for vector systems and gene transfer methods enabling efficient introduction of exogenous genes to airway epithelia. It has thus been desired to develop vectors for efficient gene transfer to airway epithelia.

Sendai virus belonging to the family Paramyxoviridae is very useful as a vector for gene transfer, and its development is in progress (Kato, A. et al., EMBO J. 16: 578-598, 1997, WO97/16538, WO97/16539). Sendai virus shows low toxicity and expresses genes introduced therein at an extremely high level. This virus is also very safe because a gene insert in the virus vector is never integrated into the host chromosome. It has been reported that transfectionability of a Sendai virus vector is different from that of adenovirus (Goldman, M. et al., Gene Ther. 3: 811-818, 1996, Boucher, R. C., J. Clin. Invest 103: 441-445, 1999). For example, adenovirus is likely to infect injured sites, compared to uninjured sites (Kitson, C. et al., Gene Ther. 6: 534-546, 1999, Zabner, J. et al., J. Biol. Chem. 270: 18997-19007, 1995, Fasbender, A. et al., Gene Ther. 4: 1173-1180, 1997).

These reports suggest that Sendai virus can complement the defect of adenovirus.

DISCLOSURE OF THE INVENTION

An objective of the present invention is to provide a vector for introducing exogenous genes to airway epithelia and a method for introducing exogenous genes using the vector.

The present inventors investigated in vitro and in vivo gene transfer efficiency of a recombinant Sendai virus vector, adenovirus vector, and cationic lipid complex, each containing an exogenous gene, to airway epithelial cells derived from various animals. The results showed that the Sendai virus vector much more efficiently introduced the exogenous gene to airway epithelial cells than the adenovirus vector and cationic lipid complex.

The inventors also found that the recombinant Sendai virus vector efficiently introduced the exogenous genes not only to permissive mouse respiratory tracts, but also to non-permissive airway epithelial cells of large animals such as ferret, sheep, and human. Furthermore, the Sendai virus vector was found to infect submucosal glands as well as apical surfaces of epithelial cells. Based on these findings, the present invention was completed.

Specifically, the present invention provides a composition for introducing exogenous genes to airway epithelia comprising a recombinant Sendai virus vector carrying an exogenous gene.

The present invention also provides a method for introducing exogenous genes to airway epithelia, the method comprising contacting a composition comprising a recombinant Sendai virus vector carrying an exogenous gene with airway epithelia covered with mucus.

The present invention will be illustrated below in more detail.

The "recombinant Sendai virus vector" used herein means a reconstitution product of virus and virus-like particles from recombinant Sendai virus cDNA and comprises recombinant Sendai virus RNA and a Sendai virus body having infectivity. The term "infectivity" used herein means the capability of a virus to transfer its nucleic acid, etc. into cells through its adhesiveness to the cells and penetrating capability into cells via various mechanisms including fusion of the viral membrane and host cellular membrane. The recombinant Sendai virus vector can be ribonucleoprotein (RNP).

The "gene" used herein includes RNA and cDNA.

The "airway epithelial cells" means pseudostratified ciliated epithelial cells, as well as goblet and Clara cells, present on the internal surface of airways of nose, pharynx, trachea, or any conducting airway, or cells present on gas-exchange alveolar surface including type-I and II pneumocytes in lung.

The recombinant Sendai virus vector of the present invention carries a recombinant Sendai virus gene. The native Sendai virus genome consists of short 3' leader region, nucleocapsid (N) gene, phospho (P) gene, matrix (M) gene, fusion (F) gene, hemaglutinin-neuraminidase (HN) gene, large (L) gene, and short 5' trailer region in this order.

The Sendai virus gene used as a starting material for producing the recombinant Sendai virus vector can be modified by deletion or substitution as long as the reconstituted recombinant Sendai virus vector can infect airway epithelial cells and express, in the infected cells, the exogenous gene that the vector carries. For example, incomplete viruses such as DI particles (J. Virol. 68: 8413-8417, 1994) can be used.

For used in gene therapy, the preferable recombinant Sendai virus vector has infectivity but is deficient in disseminative capability. Disseminative capability can be eliminated by deleting at least one of F gene, HN gene, and M gene. Such a vector includes, for example, the gene of Sendai virus Z strain deficient only in the F gene. Additional examples are pSeV18$^+$b(+) (Yu, D. et al., Genes to Cells 2: 457-466, 1997) and pSeV(+) (Kato, A. et al., EMBO J. 16: 578-587, 1997).

The recombinant Sendai virus gene can be obtained by inserting an exogenous gene into the Sendai virus gene as described above. Any exogenous gene can be used as long as it encodes a protein to be expressed in target airway epithelial cells. For gene therapy for CF, CFTR gene (Riordan, J. R. et al., Science 245: 1066-1073, 1989), a causative gene of CF, can be used. The exogenous gene includes genes encoding naturally occurring proteins and genes obtained by modifying the above genes by deletion, substitution, or insertion and encoding proteins functionally equivalent to the naturally occurring ones. For example, U.S. Pat. No. 5,958,893 discloses a modified CFTR gene. Examples of the other exogenous genes include genes encoding α-1 antitrypsin (Long et al., Biochem 23: 4828-2837, 1984) DNase, superoxide dismutase (SOD), catalase, etc.

The recombinant Sendai virus vector carrying an exogenous gene can be prepared, for example, as described below, referring to the methods of Kato, A. et al. (EMBO J. 16: 578-587, 1997) and Yu, D. et al. (Genes to Cells 2: 457-466, 1997).

First, a DNA sample containing a cDNA base sequence of a desired gene is prepared. Preferably, the DNA sample can be electrophoretically recognizable as a single plasmid at the concentration of 25 ng/μl or higher. NotI recognition site in the target cDNA sequence should be removed in advance if it exists. Forward and reverse (antisense strand) side synthetic DNA sequences are prepared as a primer pair containing the NotI recognition enzyme cleavage site sequence; the below-mentioned transcription termination sequences (E), intervening sequence (I), and transcription start sequence (S); and a part of the target gene sequence, to amplify and recover the desired gene fragment from the sample.

As a forward side synthetic DNA sequence, optional two or more oligo DNAs are selected from the 5' side, preferably four bases free of the NotI recognition site-derived sequences, GCG and GCC, more preferably ACTT, with adding to the 3' side the NotI recognition site gcggccgc, and optional nine bases with or without a multiple of six bases as a spacer sequence. Furthermore, a sequence corresponding to 25 bases of ORF from start codon ATG of the desired cDNA, including ATG, is added to the 3' side. In this case, approximately 25 bases are selected from the desired cDNA so that the 3' end of the forward side synthetic oligo DNAs should be G or C.

As a reverse side synthetic DNA sequence, optional two or more oligo DNAs are selected from the 5' side, preferably four bases free of the NotI recognition site-derived sequences, GCG and GCC, more preferably ATCC, with adding to the 3' side the NotI recognition site gcggccgc, and oligo DNAs of an insert fragment for adjusting the length. The length of this oligo DNAs is designed so that the total number of the complementary strand bases of cDNA and EIS bases derived from Sendai virus genome, including the NotI recognition site gcggccgc, becomes a multiple of six (so-called "rule of 6"; Kolakofski, D. et al., J. Virol. 72: 891-899, 1998, Calain, P. and Roux, L., J. Virol. 67: 4822-4830, 1993). The 3' end of the reverse side synthetic oligo DNAs is prepared by adding to the 3' side of the insert fragment the complementary strand sequence of S sequence of Sendai virus, preferably 5'-CTTTCACCCT-3' (SEQ ID NO: 1), I sequence, preferably 5'-AAG-3', and the complementary strand sequence of E sequence, preferably 5'-TTTTTCTTACTACGG-3' (SEQ ID NO: 2), a complementary sequence ending in either G or C, corresponding to 25 bases reversibly counted from a stop codon of the desired cDNA sequence.

The standard method using ExTaq polymerase (Takara Shuzo Co.) can be used for PCR. Preferably, Vent polymerase (NEB) is used and an amplified target fragment is digested by NotI to be inserted into the NotI site of plasmid vector pBluescript. A base sequence of the resulting PCR product is confirmed by a sequencer to select plasmids with a correct sequence. The selected plasmid is inserted into NotI site of a genomic cDNA plasmid of Sendai virus, such as pSeV18+b(+) (Yu, D. et al., Genes to Cells 2: 457-466, 1997) or pSeV(+) (Kato, A. et al., EMBO J. 16; 578-587, 1997), cleaved by NotI, to obtain recombinant Sendai virus cDNA to which an exogenous cDNA is inserted. Alternatively, the recombinant Sendai virus cDNA can be obtained by directly inserting into the NotI site without using plasmid vector pBluescript.

A recombinant virus vector can be obtained by transcribing the recombinant Sendai virus cDNA prepared as described above in vitro or in cells to reconstitute the virus. A virus can be reconstituted from cDNA by the known method (WO97/16538, WO97/16539).

Reconstitution from cDNA can be performed as follows.

Monkey kidney derived cell line LLCMK2 is cultured to be 70% to 80% confluent ($1 \times 10^6$ cells) in minimum essential medium (MEM) containing 10% fetal calf serum (FCS) and antibiotics (100 units/ml penicillin G and 100 μg/ml streptomycin) on a 6-well plastic plate. The cells are then infected with recombinant vaccinia virus vTF7-3 expressing T7 polymerase, which is inactivated by UV irradiation (Fuerst, T. R. et al., Proc. Natl. Acad. Sci. USA 83: 8122-8126, 1986, Kato, A. et al., Genes Cells 1: 569-579, 1996), by 2 PFU/cell. One hour after the infection, the cells were further cotransfected with 60 to 2 μg, more preferably 3 to 5 μg, of the above recombinant Sendai virus cDNA and the plasmid expressing viral proteins which act trans essential for the synthesis of whole Sendai virus genome (24 to 0.5 μg of pGEM-N, 12 to 0.25 μg of pGEM-P, and 24 to 0.5 μg of pGEM-L, more preferably, 1 μg of pGEM-N, 0.5 μg of pGEM-P and 1 μg of pGEM-L) (Kato, A. et al., Genes Cells 1: 569-579, 1996) by the transfection method such as the lipofection method using Superfect (QIAGEN Inc.). The transfected cells are cultured in serum-free MEM containing 100 μg/ml of rifampicin (Sigma) and cytosine arabinoside (AraC), more preferably, 40 μg/ml of cytosine arabinoside (AraC) to determine an optimal concentration of these drugs so as to minimize cytotoxicity of vaccinia virus and maximize the recovery of the virus (Kato, A et al., 1996, Genes Cells 1: 569-579). Forty-eight hours after the transfection, the cells are recovered and disrupted by repeating freeze thaw three times, and injected into chorioallantoic cavity of 10-day embryonated chicken egg. After three days, the chorioallantoic fluid is recovered to determine the virus titer by measuring hemagglutinin activity (HA). HA can be determined by "endo-point dilution method" (Kato, A. et al., 1996, Genes Cells 1: 569 579). The samples from which HA has not been detected are further injected into embryonated chicken eggs. The titer of Sendai virus to be recovered is usually $10^8$ to $10^9$ PFU/ml and that of the vaccinia virus vTF7-3 contained together is $10^3$ to $10^4$ PFU/ml or lower. The samples are diluted 106 fold and multiplied again in chicken eggs to remove the vaccinia virus. The recombinant viruses obtained through the second or third passage in the embryonated chicken eggs are stored to obtain recombinant virus vectors into which the desired cDNA is inserted. Plaque forming potential of the stored virus is generally $10^9$ PFU/ml or 10,240 HA unit/ml, and this value will be kept if the virus is stored at −80%.

Host cells used for reconstitution are not particularly limited as long as the recombinant Sendai virus cDNA can reconstitute in the cells. Cell lines used as hosts includes cultured cells such as CV-1 cells derived from monkey kidney and BHK cells derived from hamster kidney as well as LLCMK2 cells, and cells of human origin.

The reconstituted recombinant Sendai virus can be bound to adhering molecule, ligand, receptors, etc. on its envelope surface for facilitating the adherence to specific cells.

The above-described chorioallantoic fluid containing the virus vector can be used as the composition comprising the recombinant Sendai virus vector of the present invention.

The composition of the present invention can comprise any physiologically acceptable medium such as deionized water, 5% dextrose in water, and the like. Other auxiliary components may be included in the composition such as stabilizers, biocides, etc. The composition comprising the recombinant Sendai virus vector can be in lyophilized dosage form. Such a composition can further comprise, in addition to the above-described auxiliaries, stabilizers such as albumin, Prionex™ (Pentapharm, Japan), or the like.

The exogenous gene contained in the recombinant Sendai virus can be introduced into airway epithelial cells by contacting the composition containing the recombinant Sendai virus vector with airway epithelial cells covered by mucus. When cationic lipid is used for gene transfer to airway epithelial cells, the airway mucus is a serious barrier to cationic lipid-mediated gene transfer and the mucus must be removed for introducing exogenous genes. In contrast, the composition containing the Sendai virus vector of the present invention can readily introduce exogenous genes by merely contacting it with airway epithelial cells with mucus.

The method for introducing exogenous genes of the present invention can be used for gene therapy by expression of exogenous genes that is expected to treat the disorder of airway epithelial cells, or endogenous genes encoding proteins deficient in the cells. For example, the composition of the present invention containing the virus vector carrying the CFTR gene can be useful for therapy of CF. Gene therapy can be performed by applying the virus vector-containing composition of the present invention to airway epithelial cells of diseased sites in vivo or ex vivo and allowing exogenous genes to express in the cells. In vivo gene transfer can be carried out by local application such as instillation or inhalation using nebulizers to nasal cavity or lung. Examples of nebulizers include those commercially available and typically used in the treatment of asthma.

The virus vector-containing composition of the present invention can be applied to any mammals including human, mouse, rabbit, sheep, bovine, monkey, etc.

BRIEF DESCRIPTION OF DRAWINGS

FIG. 10 shows gene transfer efficiency of the recombinant Sendai virus vector of the present invention and a cationic lipid complex to mucin-added sheep tracheal cells. F indicates fresh cells and MD mucus-depleted cells. Error bars indicate SEM.

BEST MODE FOR CARRYING OUT THE INVENTION

Figure 1:
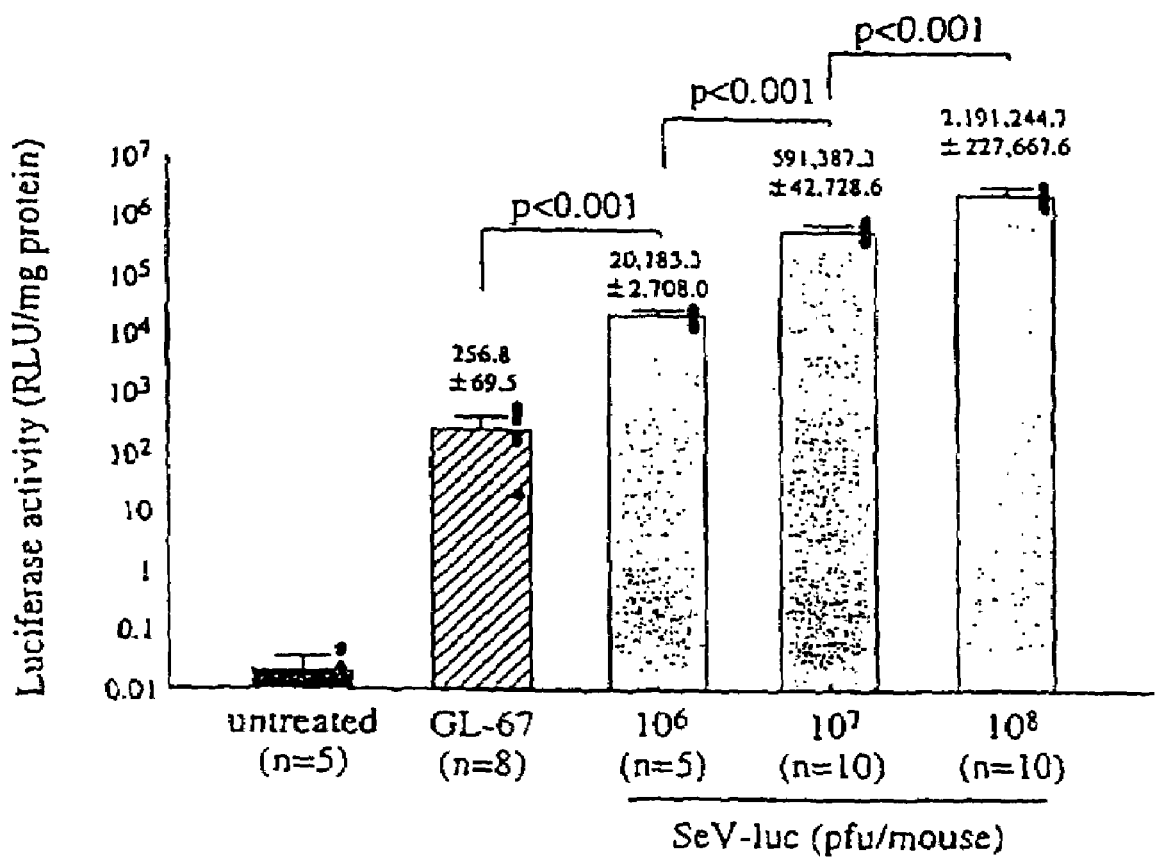
FIG. 1 shows in vivo gene transfer efficiency of the recombinant Sendai virus vector of the present invention and a cationic lipid complex in mouse lung and nose. Error bars indicate SEM.
Figure 2:
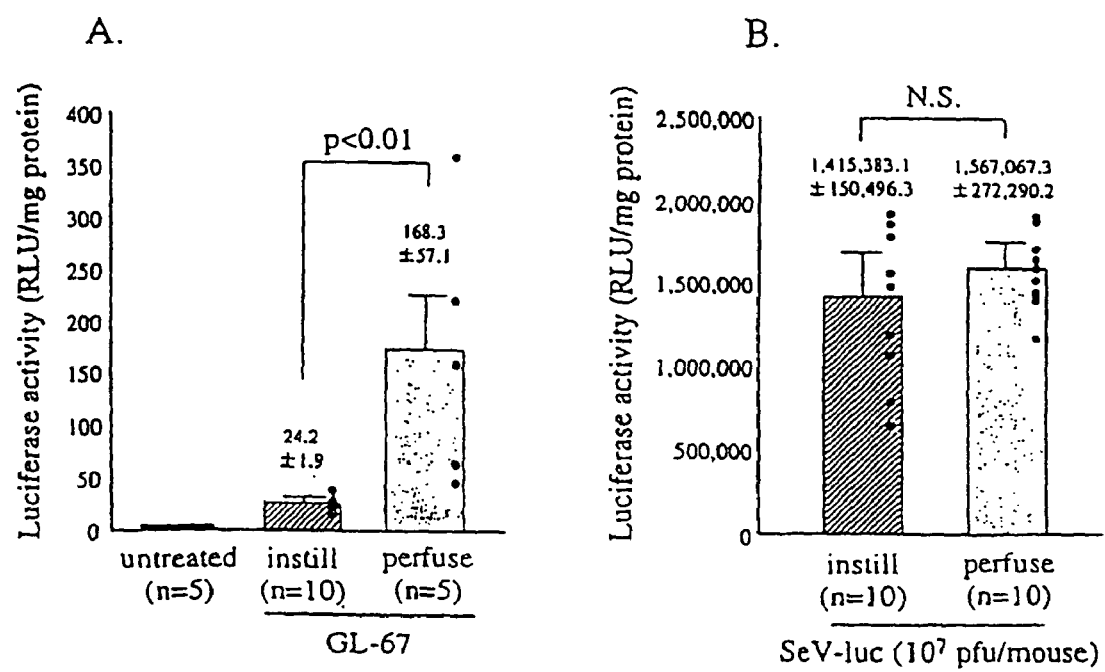
FIG. 2 shows effect of contact time on gene transfer efficiency of the recombinant Sendai virus vector of the present invention (A) and a cationic lipid complex (B) in mouse nose assessed by nasal instillation (brief contact) and perfusion (longer contact). Error bars indicate SEM.

The present invention will be illustrated with reference to the following examples, but is not construed as being limited thereto.

EXAMPLE 1

Construction and Reconstitution of Recombinant Sendai Virus Vector

A recombinant Sendai virus was constructed by the known method (Kato, A. et al., EMBO J. 16: 578-598, 1997, Hasan, M. K. et al., J. Gen. Verol. 78: 2813-2810, 1997). First, 18 bp of spacer sequence (5'-(G)-CGGCCGCA-GATCTTCACG-3') (SEQ ID NO: 3) with the NotI restriction site was inserted into the proximal locus between the leader sequence and the 5'-end of the sequence encoding N-protein of cloned SeV genomic cDNA, pSeV(+), to obtain plasmid pSeV18⁺b(+), which also contains a self-cleaving ribozyme site from antigenomic strand of hepatitis delta virus. Whole cDNA of E. coli lacZ containing nuclear localising signal, luciferase, green fluorescent protein (GFP), and E. coli lacZ were amplified by polymerase chain reaction using the primers with the NotI site and new sets of SeVE and S signal sequence-tags for exogenous genes, and inserted into the NotI site of the cloned genome. The whole length of template SeV genomes with exogenous genes were arranged to multiple of six nucleotides. Template SeV genome with exogenous gene, plasmids encoding N-, P- and L-proteins (pGEM-N, pGEM-P, pGEM-L) were complexed with commercially available cationic lipids, GL-67-DOPE-PEG (Genzyme Co. Ltd.) and co-transfected with vaccinia virus vT7-3 (Fuerst, T. R. et al., Proc. Natl. Acad. Sci. USA 83: 8122-8126, 1986, Kato, A. et al., Genes Cells 1: 569-579, 1996) to LLCMK2 cells. Forty hours later, the cells were disrupted by 3-cycles of freezing and thawing, and injected into the chorioallantoic cavity of 10-day-old embryonated chicken eggs. Then the virus was recovered and the vaccinia virus was eliminated by second passage in eggs. Virus titer was determined by hemagglutination assay (HA) (Kato, A. et al., Genes Cells 1: 569-579, 1996) using chicken red blood cells, and the chorioallantoic fluid containing the viruses were kept freeze at −80° C. just before use to serve as the composition containing the recombinant Sendai virus vector of the present invention.

EXAMPLE 2

In vivo Gene Transfer to the Mouse Nose and Lung by Nasal Instillation or Nasal Perfusion

2-1. Comparing Sendai Virus Vector with Cationic Lipid pCMV-luciferase was constructed by insertion of HindIII-BamHI fragment of pGL3-control vector (Promega), into the multicloning site of pcDNA3 (Invitrogen) to be driven by human cytomegalovirus immediate early (CMV-IE) promoter. pCMV-luciferase was then complexed with GL-67-DOPE-PEG (Genzyme Co. Ltd.) to obtain GL-67-pCMV-luc.

To examine gene transfer efficiency of the vectors to the lung and the effect of contact time on gene transfer efficiency, the vectors were administered to nasal cavity by nasal instillation and nasal perfusion. First, male balb/c mice (6-8 weeks) were instilled intranasally with 100 µl of various concentration of the Sendai virus vector containing luciferase (SeV-luc) prepared in Example 1 or GL-67-pCMV-luc (80 µg DNA/mouse) by the known method (Yonemitsu, Y. et al., Gene Ther. 4: 631-638, 1997).

Nasal perfusion was performed by intranasally inserting 5 mm of a catheter, and perfusing 15011 each of vector solution at rate of 5 to 6 µl/minutes using Peristaltic pump (model P-1, Pharmacia Biotech). Two days after gene transfer, the mice were killed under the sufficient anesthesia by intraperitoneal injection of overdose pentobarbitar, and turbinates, trachea, and lung were harvested and subjected to luciferase assay.

As a control, pSeV18b+ used in Example 1 was subjected to the same gene transfer procedure as described above. This plasmid was used as a control in the following examples.

Luciferase assay was performed as follows according to the known method (Yonemitsu, Y. et al., Gene Ther. 4: 631-638, 1997). First, tissues were washed with PBS and minced with scissors in the 1× lysis buffer with protease inhibitor cocktail, centrifuged at 13,000 rpm for 10 minutes at 4° C. and 30 µl of the supernatant was subjected to 1001 of luciferase assay buffer (Promega). The light intensity was measured by Turner TD20e luminometer (Turner Co.) with 10 seconds integration soon after 10 seconds preincubation at 20° C. In this condition, 1 pg of recombinant luciferase (Promega) is equivalent to $2.56 \times 10^1$ RLU. The protein concentration was measured by Bradford's method using commercially available protein assay system (Bio-Rad Laboratories Ltd., Hertfordshire, UK) according to standard curve correspond to bovine serum albumin. The data was expressed as RLU/mg protein, and each samples were measured more than twice.

FIGS. 1 (lung) and 2 (nose) show comparison of gene transfer efficiency between SeV-luc and GL-67-p-CMV-luc. As shown in FIG. 1, SeV-luc transfected lungs exhibited more than 1,000-fold higher luciferase activity than that of GL-67-pCMV-luc dose-dependently. Luciferase gene expression by SeV showed approximately 10,000-times greater than GL-67-pCMV-luc without significant difference between different contact time. These results suggest that the SeV vector enables efficient gene transfer to mouse lung and nose by merely contacting the vector with airway epithelia.

2-2. Comparing Sendai Virus Vector with Adenovirus Vector

SeV-lucor adenovirus vector containing a luciferase gene, AdCMV-luciferase (Ade-luc) (Kendall, J. M. et al., Cell Calcium 19: 133-142, 1996) was instilled intranasally in the same manner as in Example 1, turbinates, trachea, and lung were harvested and subjected to luciferase assay.

Sendai virus vector and adenovirus vector both carrying lacZ gene with nuclear localizing signal of simian virus large T antigen (SeV-NLS-lacZ and AdCMV-nls-lacZ) were prepared and subjected to nasal instillation in the same manner as described in 2-1. Bronchi, tracheae, and turbinates were harvested. Each tissue was fixed with ice-cooled 2% paraformaldehyde with 0.25% glutaraldehyde in 0.1M PBS for 10 minutes and followed by X-gal staining (solution: 5 mM potassium ferrous cyamide, 5 mM ferric cyamide, 2 mM magnesium chloride, 1 mg/ml 5-bromo-4-chloro-3-indolyl-β-D-galacto-pyranoside) for 3 hours at room temperature under rotate shaker. The X-gal stained tissue was refixed and mounted to paraffin, and 5 µm sections were examined under light microscope. The results are shown in FIGS. 3, 4, and 5.

Figure 3:
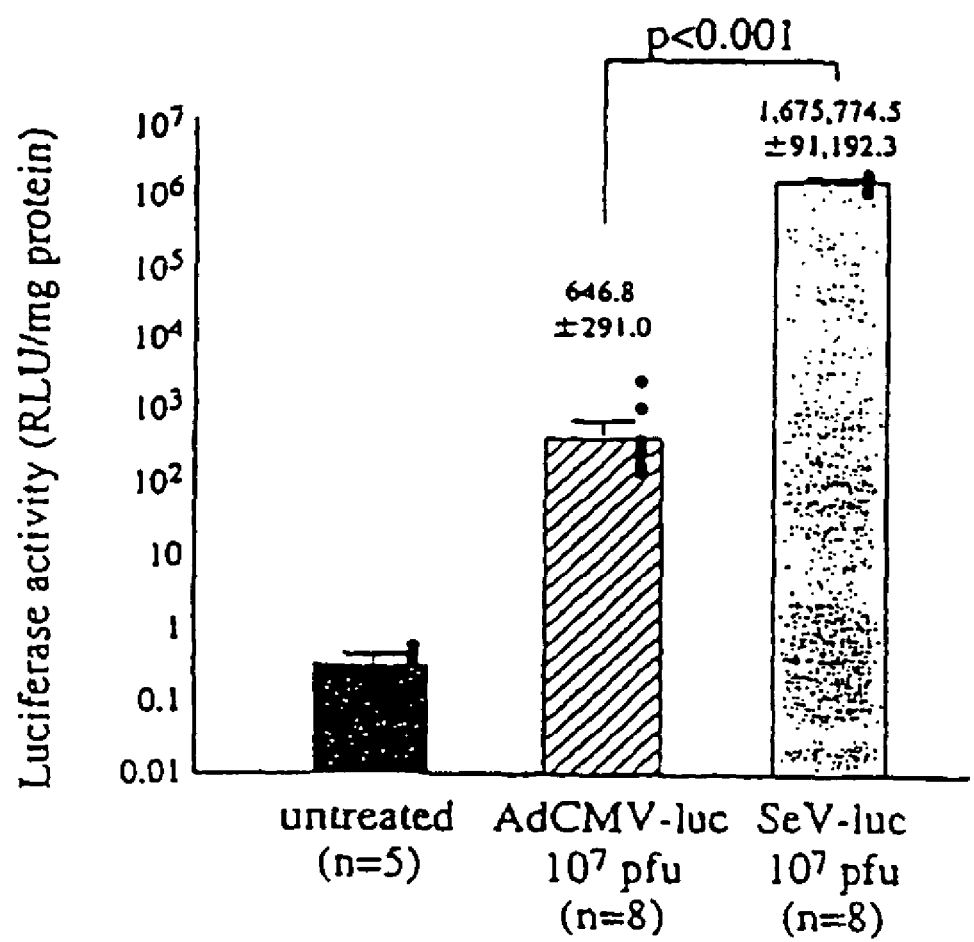
FIG. 3 shows gene transfer efficiency of the recombinant Sendai virus vector of the present invention and the adenovirus vector in mouse nose assessed by nasal instillation. Error bars indicate SEM.

As shown in FIG. 3, SeV-luc transfected cells demonstrated 5,000-times greater gene expression than that of Ade-luc.

Figure 4:
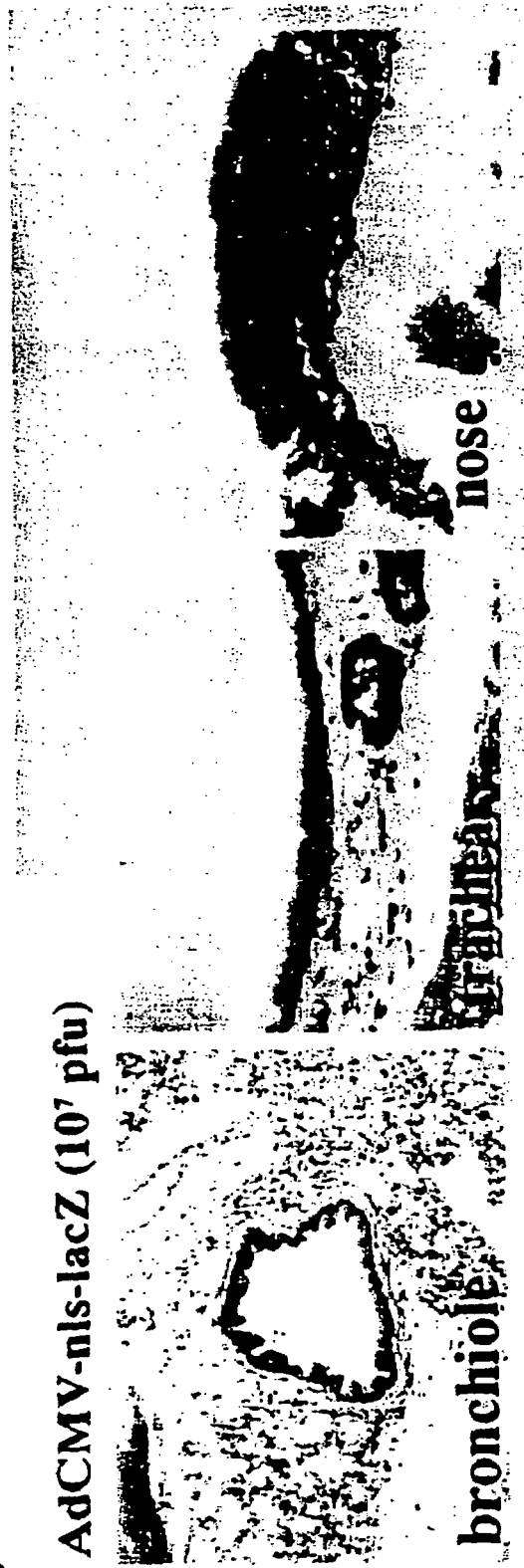
FIG. 4 shows microscopic photographs detecting by X-gal staining β-gal gene expression in mouse bronchile, tranchea, and nose introduced by nasal instillation of the recombinant Sendai virus vector of the present invention and the adenovirus vector.
Figure 5:
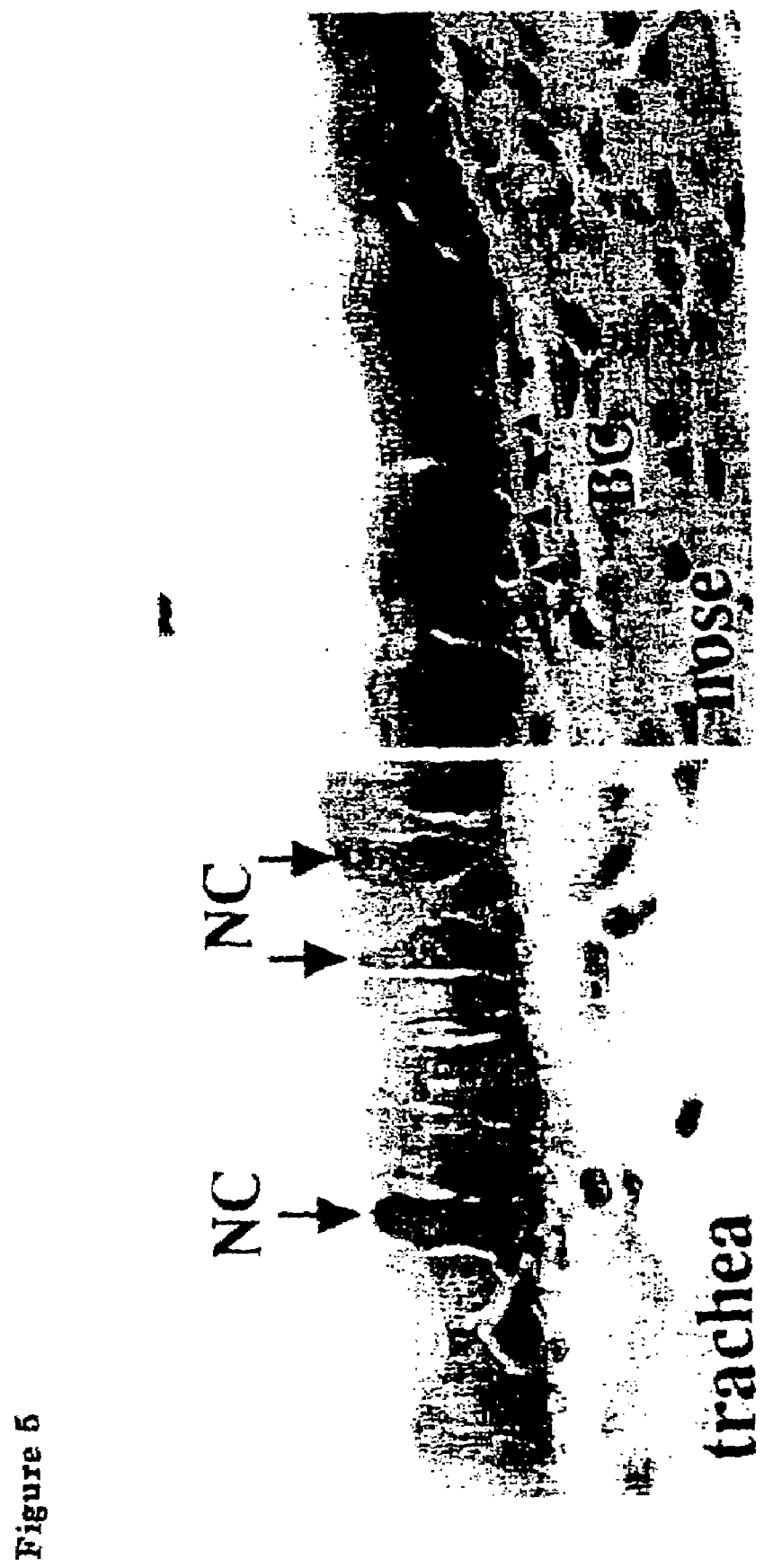
FIG. 5 shows microscopic photographs detecting by X-gal staining gene expression in mouse tranchea and nose of β-gal introduced by nasal instillation of the recombinant Sendai virus vector of the present invention and the adenovirus vector. NC indicates non-ciliated secretory cells and BC basal cells.

X-gal positive epithelial cells were scattered in the bronchioli in similar frequency in both vector innoculation (FIG. 4). On the other hand, X-gal positive cells were frequently observed in SeV-NLS-lacZ treated animals, while blue cells were rare in the trachea or nose of AdCMV-nls-lacZ treated mice. As shown in FIG. 5, blue stains were seen not only in ciliated columnar cells but also non-ciliated secretary cells (NC). In contrast, no detectable blue signals were seen in basal cells (BC).

These results reveal that Sendai virus vectors enable gene transfer to airway epithelial cells to which adenovirus vectors cannot introduce genes.

EXAMPLE 3

Gene transfer to Lung of Ferret

Ferrets (500-600 g weight) were anaesthetised and instilled intranasally with 3 ml of purified SeV-LacZ in BSS with either $3 \times 10^8$ or $3 \times 10^9$ pfu/ml (n=3 each group), as in Example 2. Controls (n=2) received 3 ml of SeV-Luc ($10^9$ pfu/ml). Forty-eight hours post-infection, ferrets were sacrificed, the trachea cannulated in situ and the lungs inflated with ice cold fixative solution (2% formalin, 0.2% glutaraldehyde, 2 mM $MgCl_2$, 5 mM EGTA in PBS, pH 7.3). The trachea and lungs were excised en bloc and underwent X-Gal staining as described in Example 2. Each lung was dissected into 7 parts: trachea, 4 right lobes (upper (R1), mid (R2, R3), and lower (R4)) and 2 left lobes (upper (L1) and lower (L2)), and β-gal positive cells in the airway epithelia and submucosal glands were quantified microscopically by point counting using a graticulated lens. Ten ×20 magnification fields/airway were assessed to obtain the percentage of blue cells/airway and 3 to 8 airways randomly taken from different regions of a lobe (proximal, medium and distal) were assessed for each lobe. For submucosal glands, 10 to 28 fields (containing at least 4 glands)/lobe were assessed. The error of repeat measurement (ERM) expressed as a coefficient of variation (CV) was 18%. Intra-animal CV was between 24 and 43% for animal receiving $10^8$ pfu/ml and between 8 and 14% for animals receiving $10^9$ pfu/ml.

Figure 6:
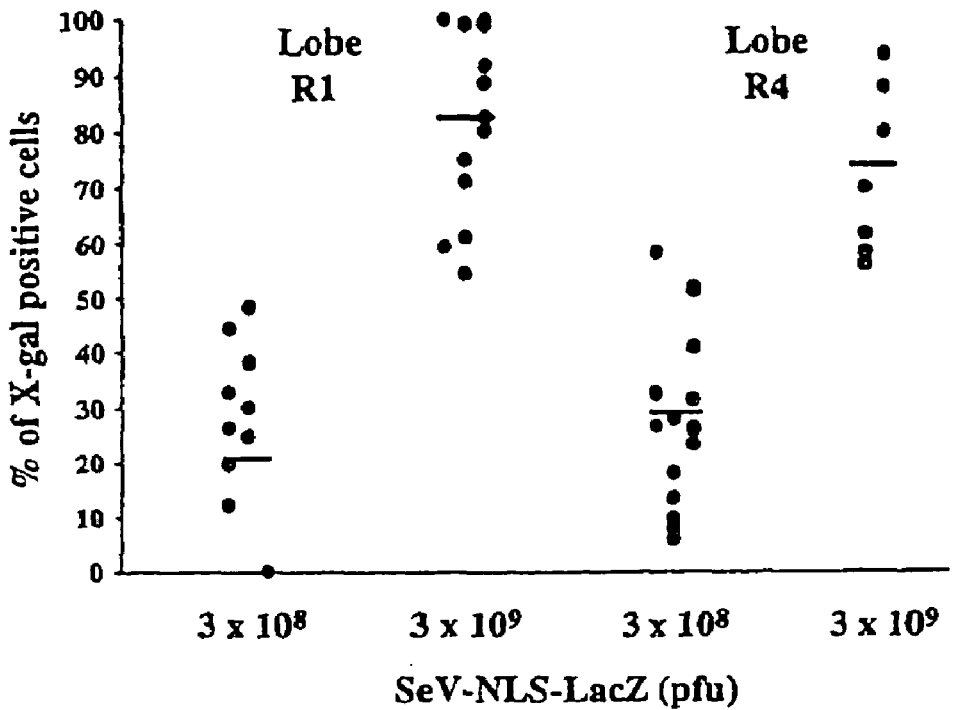
FIG. 6 shows gene expression in the airway epithelia (A) and submucosal glands (B) of ferret lung of β-gal introduced by nasal instillation of the recombinant Sendai virus vector of the present invention. R1 indicates upper right lobe, R4 indicates lower right lobe and L1 indicates upper left lobe.
Figure 6:
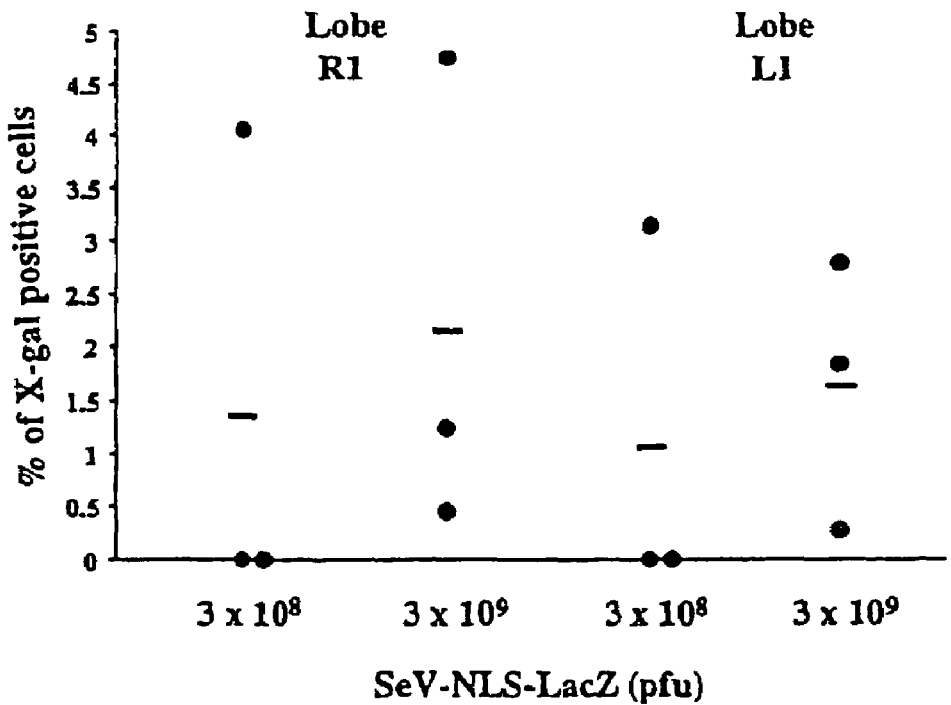
Figure 7:
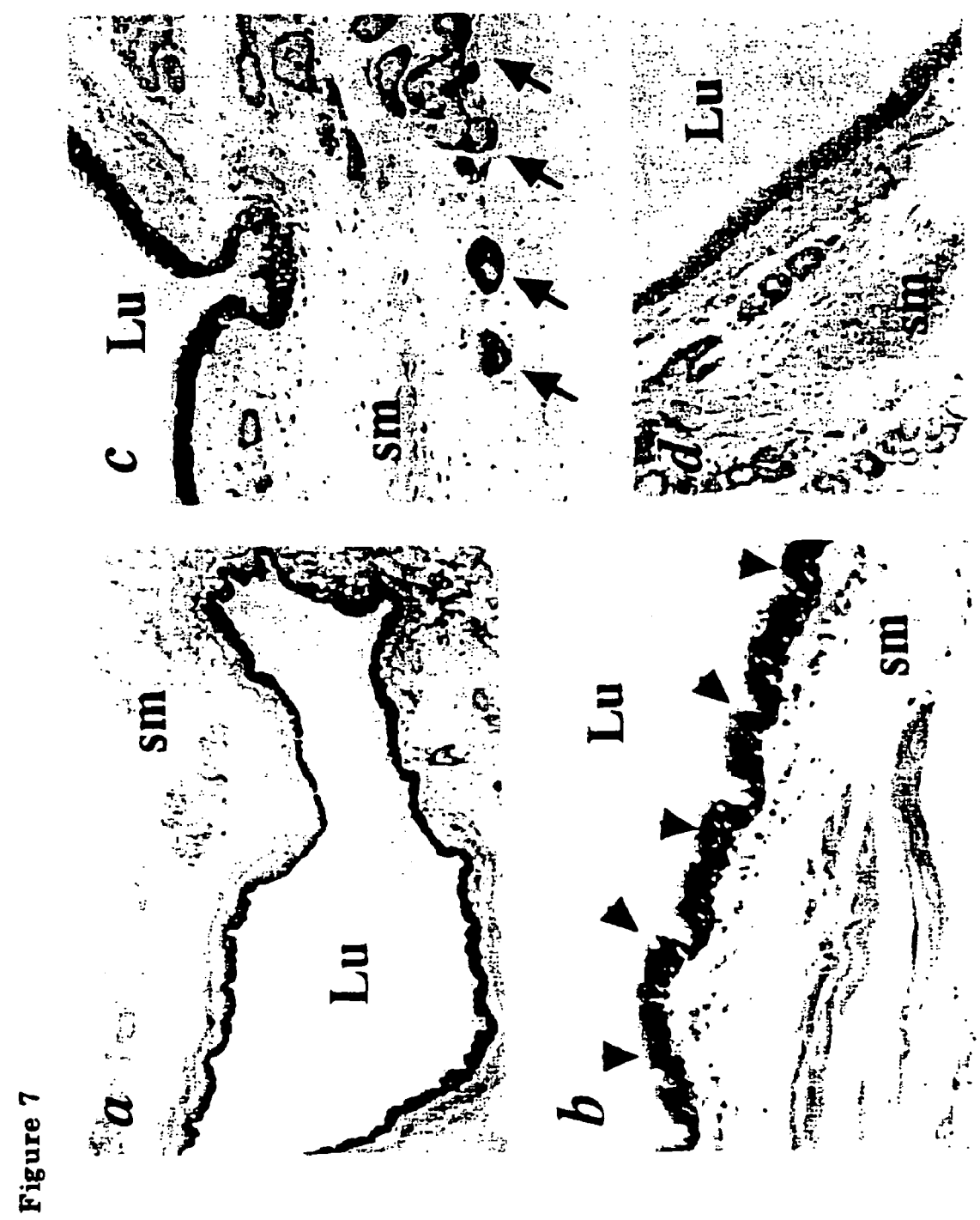
FIG. 7 shows microscopic photographs detecting gene expression of in ferret lung of β-gal introduced by nasal instillation of the recombinant Sendai virus vector of the present invention. Photograph a is for upper left lobe, b mid right lobe, c submucosal glands, and d control. Furthermore, Lm indicates bronchial cavity and sm submucosal glands.

The airway epithelia (FIG. 6A and FIGS. 7a and b) and submucosal glands (FIG. 6B and FIG. 7c) were exhibited β-galactosidase activity dose-dependently. Submucosal glands are the predominant sites of CFTR expression. No activity was found in control (FIG. 7d).

EXAMPLE 4

Gene transfer to Nasal Epithelial Cells from Human Healthy Donors

Figure 8:
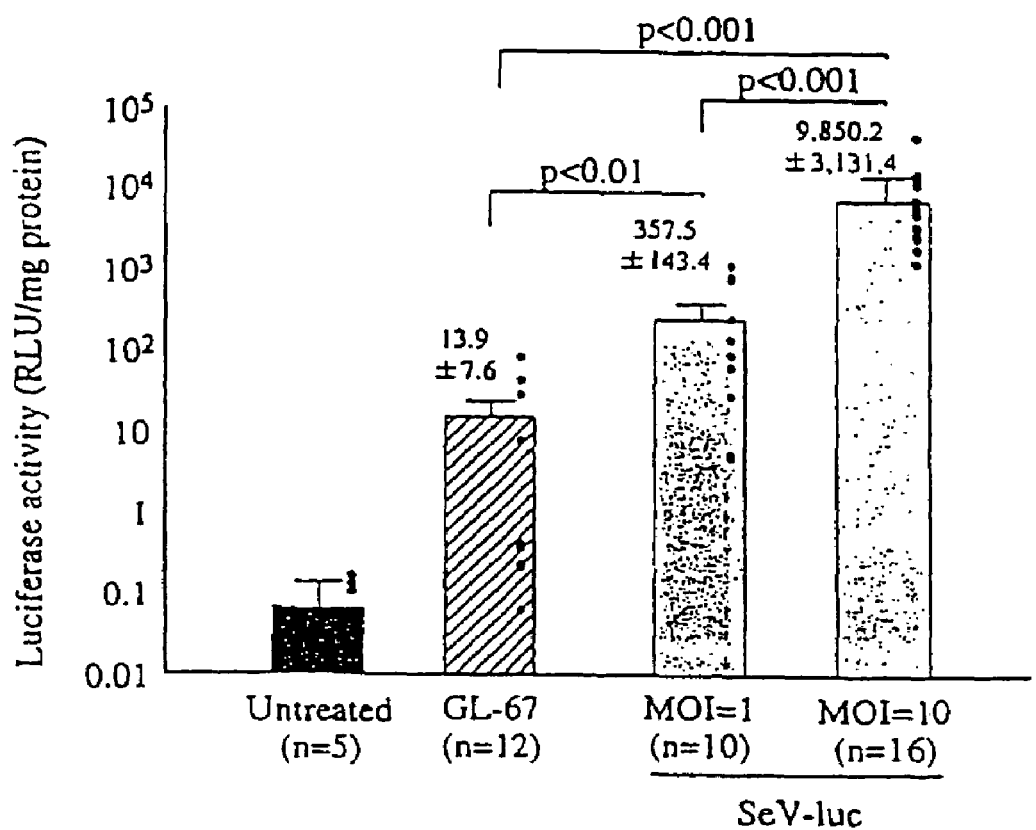
FIG. 8 shows gene transfer efficiency of the recombinant Sendai virus vector of the present invention and a cationic lipid complex to human nasal epithelial cells collected from human healthy donors. Error bars indicate SEM.

Nasal epithelial cells were collected by brushing from human healthy donors (6: male and 3: female). After 2-times wash with phosphate buffered saline (PBS: 137 mM NaCl, 3 mM KCl, 8 mM $Na_2HPO_4$, 1 mM $KH_2PO_4$, pH7.2), the cells were resuspended in the culture medium (Dulbecco's modified Eagle's medium; DMEM) with 10% bovine fetal serum, divided into 2 or 3 groups, and placed in the each wells of 96-culture plate. The viability of the nasal cells were confirmed by phase-contrast microscopic observation of ciliary beating and microscopic count of trypan blue-positive cell numbers. Vector solutions (SeV-luc and GL-67-pCMV-luc) were added to each well. Twenty four hours later, the cells were collected, washed 3-times with PBS, and subjected to luciferase assay as described in Example 2. The results are shown in FIG. 8.

SeV-luc transfected cells demonstrated about 1,000 times greater luciferase activity than that of GL-67-pCMV-luc transfected cells.

EXAMPLE 5

Gene Transfer to the Sheep Tracheal Epithelia 5-1. Effect of Mucus on Gene Transfer Effect of mucus on gene transfer efficiency of each vector was examined using a sheep tracheal strip model, which was prepared by a known method (Kitson, C. et al., Gene Ther. 6: 534-546, 1999). After killing, the epithelial layer of resected sheep trachea was dissected to muscle and adventitia, and was cut into 0.5 $cm^2$ square pieces subsequently confirmed the ciliary beating under the phase-contrast microscope. In some tissue, mucus depletion was followed to the known method (Kitson, C. et al., Gene Ther. 6: 534-546, 1999). These tissues were placed in the air-liquid interface. Ten μl of SeV-luc or GL-67-luc vector solution was applied to the apical surface to perform transfection. After 48 hours, the pieces were subjected to luciferase assay as described in Example 2. The results are shown in FIG. 9.

Figure 9:
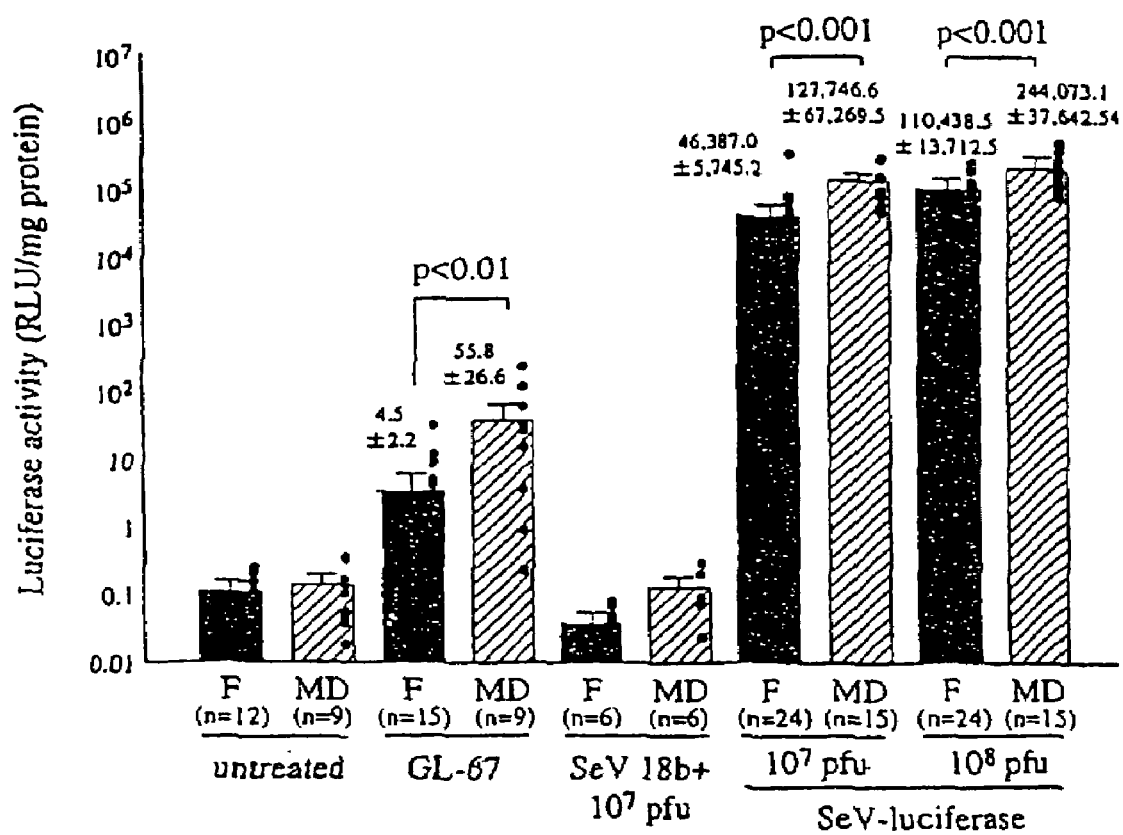

As shown in FIG. 9, mucus was not markedly affect SeV-mediated gene transfer compared to GL-67-luc-mediated gene transfer.

5-2. Effect of Viscosity of Mucus on Gene Transfer

The procedure of 5-1 was repeated except that various concentrations of bovine salivary gland mucin were applied just before gene transfer. The results are shown in FIG. 10.

Figure 10:
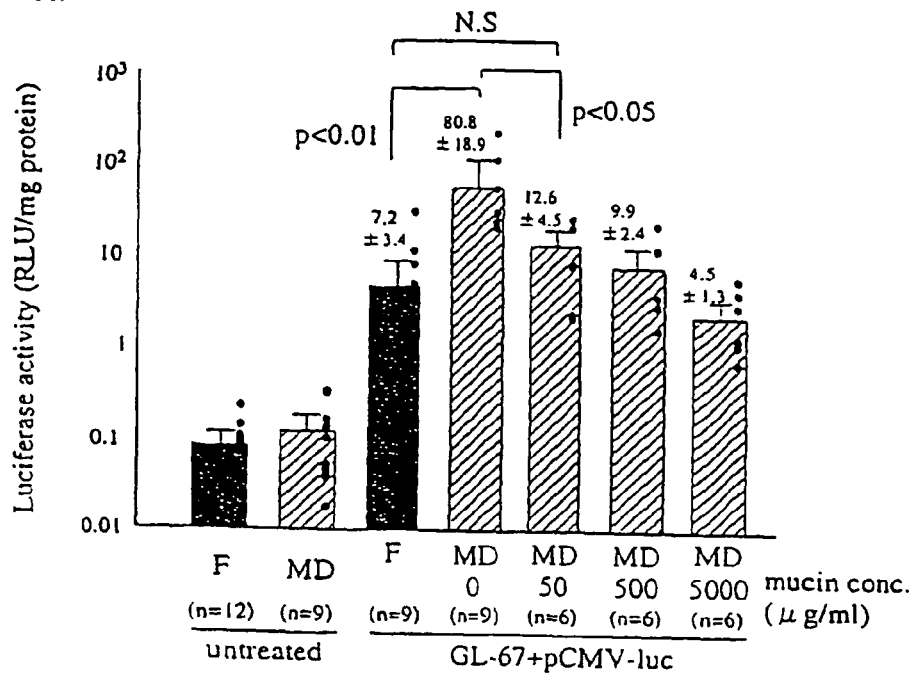
FIG. 10 shows gene transfer efficiency of a recombinant Sendai virus vector of the present invention, SeV-luc (B) and a cationic lipid complex, GL-67+pCMV-luc (A) to mucin-added sheep tracheal cells. F indicates fresh cells and MD mucus-depleted cells. Error bars indicate SEM.
Figure 10:
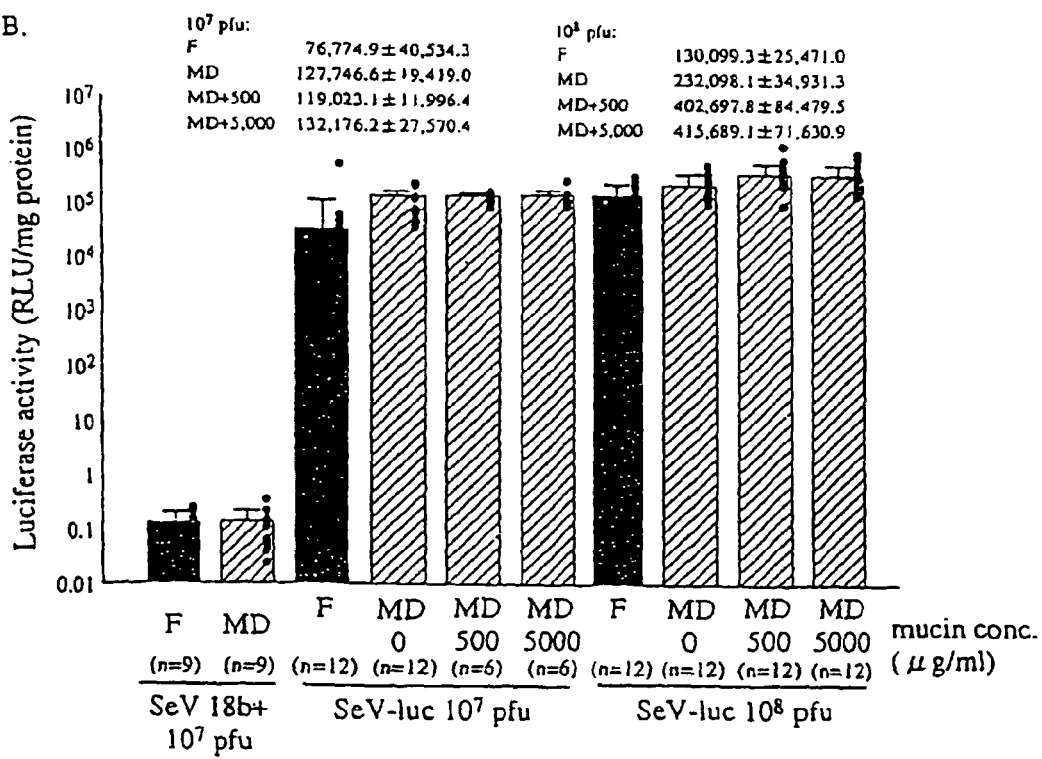

As FIG. 10 shows, gene transfer of GL-67-luc was inhibited by addition of mucin. Luciferase activities of the mucin added samples were not significantly different from that of fresh samples, suggesting barrier activity of the mucin, but not mucus viscosity, to cationic lipid-mediated gene transfer. On the other hand, serous mucin components do not affect SeV infection efficiency, while mucus viscosity mildly affect to SeV-mediated gene transfection.

5-3. Site-Specific Transfection Efficiency

Figure 11:
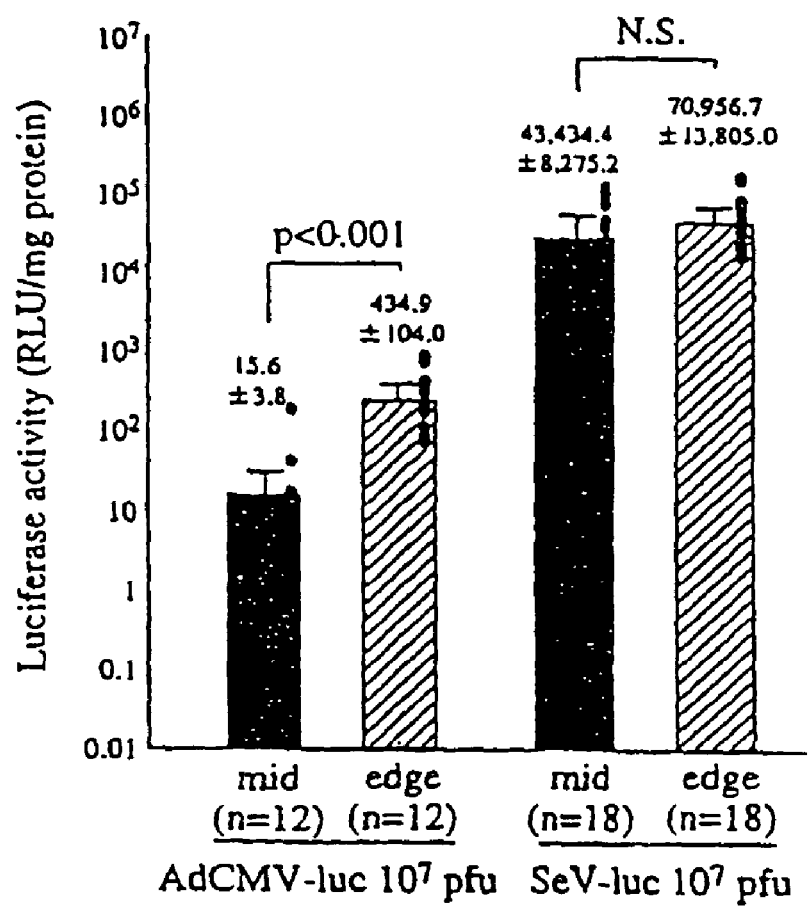
FIG. 11 shows gene transfer efficiency of the recombinant Sendai virus vector of the present invention and the adenovirus vector to edge and mid portions of sheep tracheal cells. Error bars indicate SEM.

Sheep tracheal epithelia were transfected with SeV-luc or AdCMV-luc in the same manner as in 5-1. After gene transfer, the edge of the tissue was dissected and cut, and the luciferate activity of edge and mid portion was measured separately. The results are shown in FIG. 11. The same gene transfer procedure as above was repeated using SeV-GFP and high titer adenovirus serotype 5 carrying GFP driven by CMV-IE promoter, AdCMV-GFP (Kramel Biotech International Ltd.), in place of SeV-luc and AdCMV-luc. Two days after gene transfer, green fluorescent protein (GFP) signals were observed under fluorescent phase-contrast microscope. The results are shown in FIG. 12.

Figure 12:
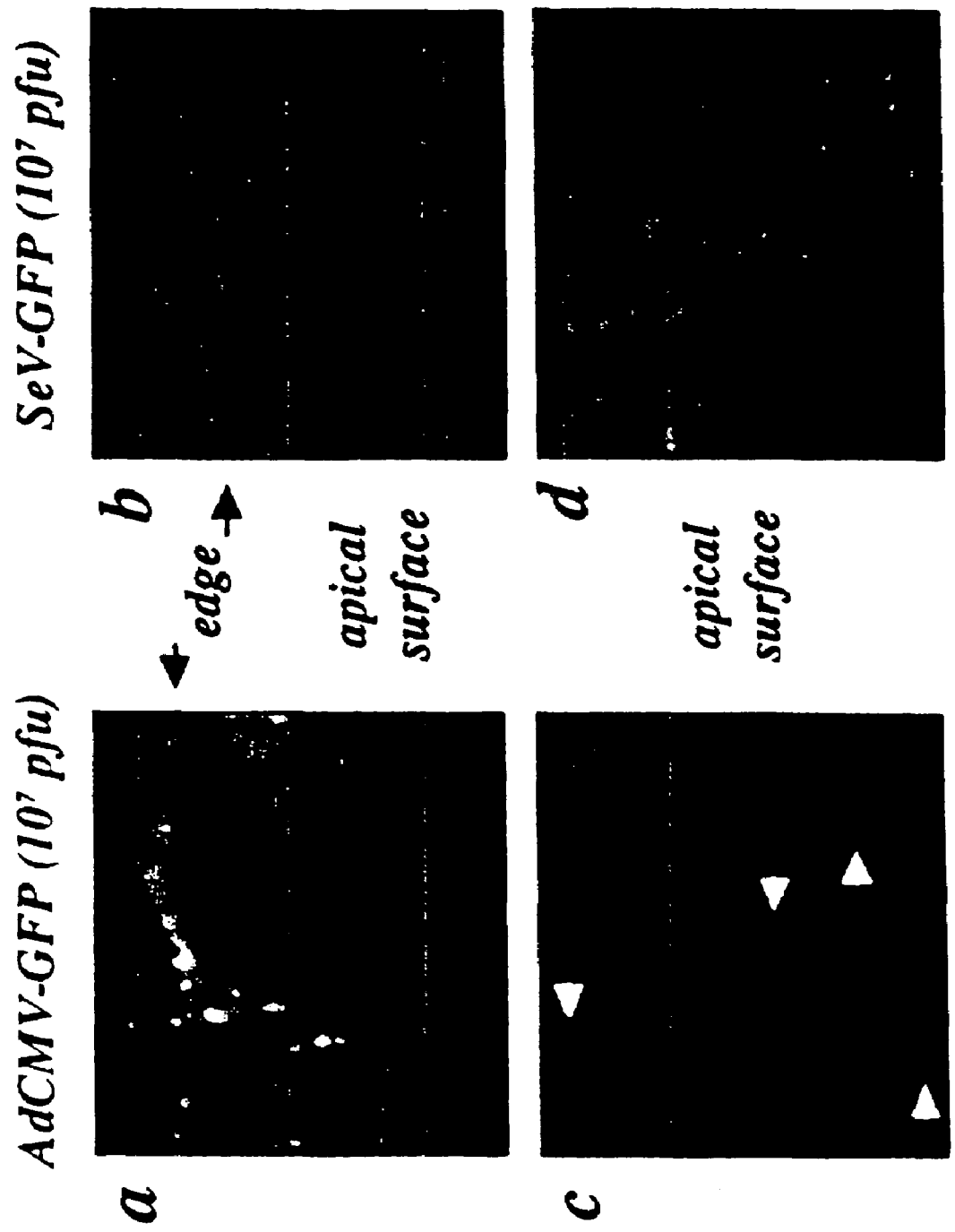
FIG. 12 shows microscopic photographs detecting signals of GFP introduced by a recombinant Sendai virus vector of the present invention, SeV-CFP (b: edge; d: mid portion), and an adenovirus vector, AdCMV-GFP (a: edge; c: mid portion), to sheep tracheal cells.

As shown in FIGS. 11 and 12, AdCMV-luc showed higher expression in injured edge, while relatively little expression in uninjured mid-portion of sheep tracheal tissue. In contrast, SeV-luc-treated tissue showed no significant difference in gene expression between edge and mid portions.

EXAMPLE 6

Construction of SeV/CFTR and Electrophysiological Characterization

A recombinant Sendai virus vector expressing CFTR, the causative gene of CF, was constructed. CFTR gene (Riordan, J. R. et al., Science 245: 1066-1073, 1989) was amplified by PCR using a primer set containing E and S signal sequences. The primer set used are as follows.

Forward primer: 5'-acttgcggccgccaaagttcaatgcagaggtcgcctctg gaaaaggccagc-3' (SEQ ID NO: 4)

Backward primer: 5'-atccgcggccgcgatgaactttcaccctaagttttct tactacggctaaagccttgtatcttgcacctcttcttc-3' (SEQ ID NO: 5).

The amplified fragment was inserted into the NotI site of pSeV18$^+$b(+), and reconstitution of the virus was conducted as in Example 1.

Figure 13:
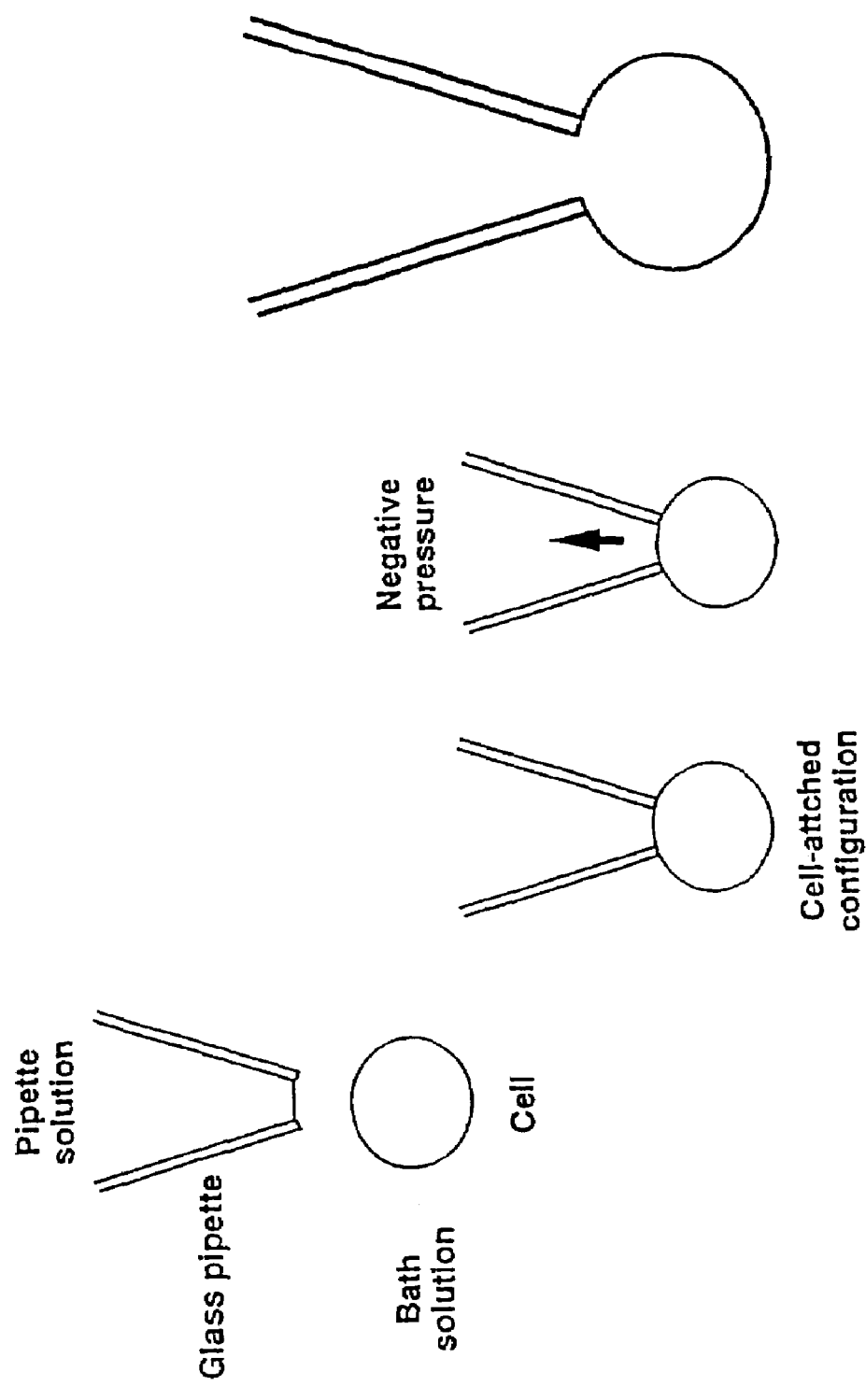
FIG. 13 schematically shows a conventional whole-cell configuration.
Figure 14:
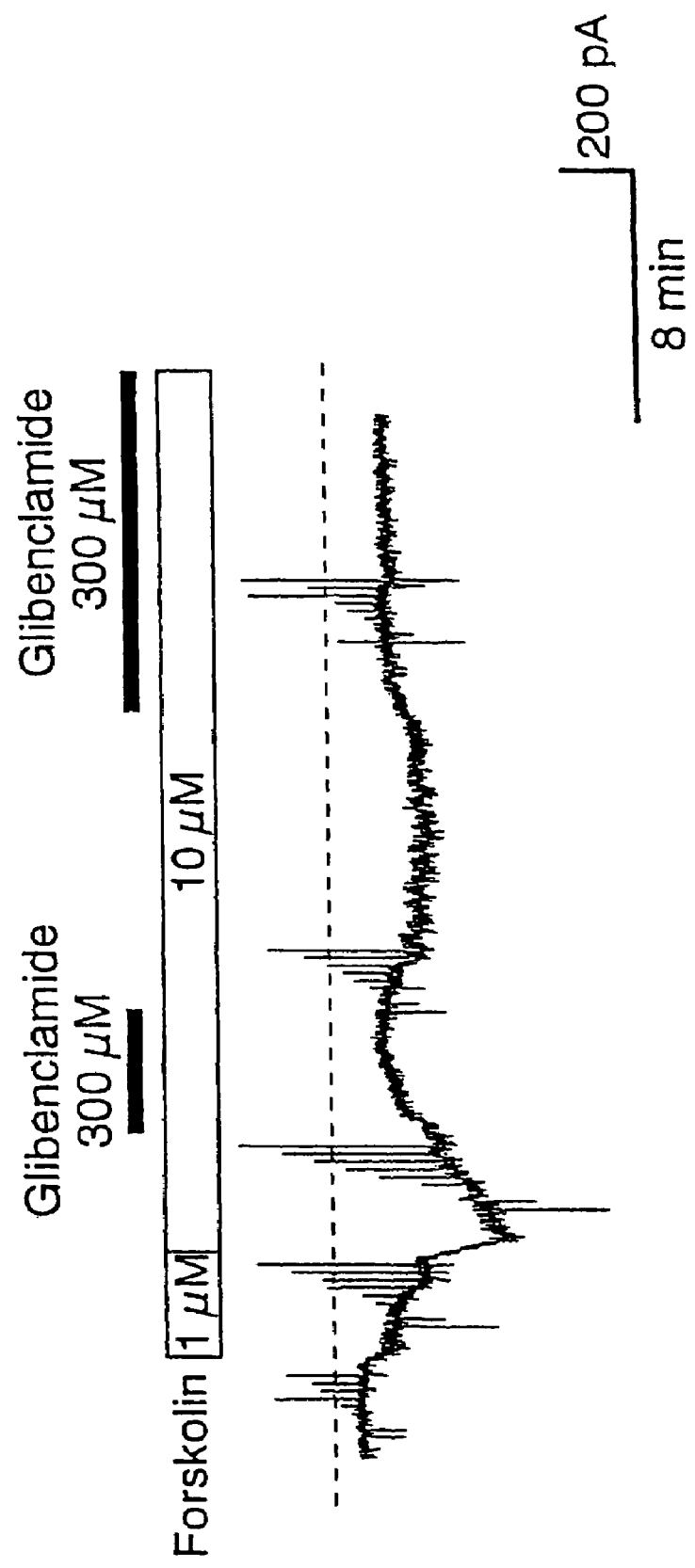
FIG. 14 shows the time course of forskolin-induced inward current at −60 mV in COS7 cells expressing sample-1 SeV/CFTR. The membrane potential was kept at a holding potential of −60 mV. The vertical deflection indicates the rectangular pulses (duration, 1 s) at 15 s intervals from −100 mV to +60 mV. The dash line indicates the zero current level.

COS7 cells were infected with the prepared CFTR-expressing Sendai virus (sample-1 SeV/CFTR), and the obtained infected cells were analyzed by the whole-cell patch clamp technique. FIG. 13 shows a summary of the whole-cell patch clamp technique. A glass pipette containing a pipette solution was contacted with a cell within a bath solution, and negative pressure was applied to remove the cell membranes. In this occasion, the pipette solution contains 145 mM $NMDG^+$, 148.4 mM $Cl^-$, 6.7 mM $Mg^{2+}$, 5 mM ATP, 10 mM glucose, 0.1 mM EGTA, and 10 mM HEPES (titrated by Tris, pH 7.4), and the bath solution contains 141 mM $Na^+$, 152.4 mM $Cl^-$, 152.4 mM $H_2PO_4^-$, 5 mM $K^+$, 1.7 mM $Mg^{2+}$, 2 mM $Ca^{2+}$, 10 mM glucose, 0.1 mM EGTA, and 10 mM HEPES (titrated by Tris, pH 7.4). The effects of forskolin on the membrane current in COS7 cells expressing sample-1 SeV/CFTR were examined by whole-cell recording (FIG. 14). As a result, a forskolin concentration-dependent influx current was observed (a downward decrease of trace), which was suppressed (an upward transition) by glibenclamide (chloride channel blocker). The influx current was reproduced by adding forskolin again after a single wash, and was again suppressed by glibenclamide, which confirmed that the observed change in current was a specific drug-induced response.

Figure 15:
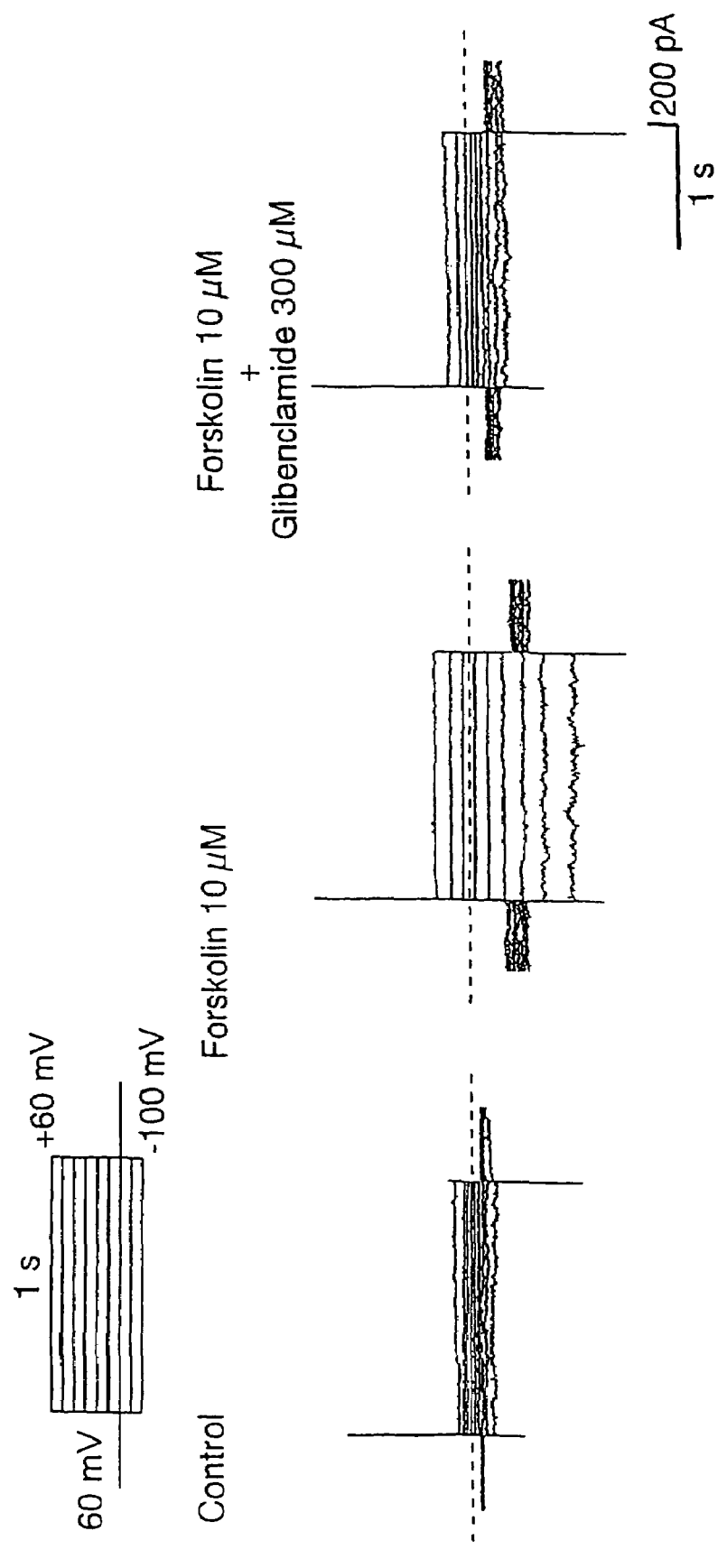
FIG. 15 shows effects of forskolin on the membrane current in COS7 cell expressing sample-1 SeV/CFTR. The membrane potential was kept at a holding of −60 mV. The dash line indicates the zero current level. Glibenclamide (300 μM) inhibited forskolin-induced Cl currents.

Next, the time-dependency of each drug-induced reaction was examined (FIG. 15). Forskolin induced a Cl⁻ current in COS7 cells expressing sample-1 SeV/CFTR, and a time-independent reaction characteristic to chloride channels was observed. Glibenclamide (300 μM) inhibited forskolin-induced Cl⁻ currents.

Figure 16:
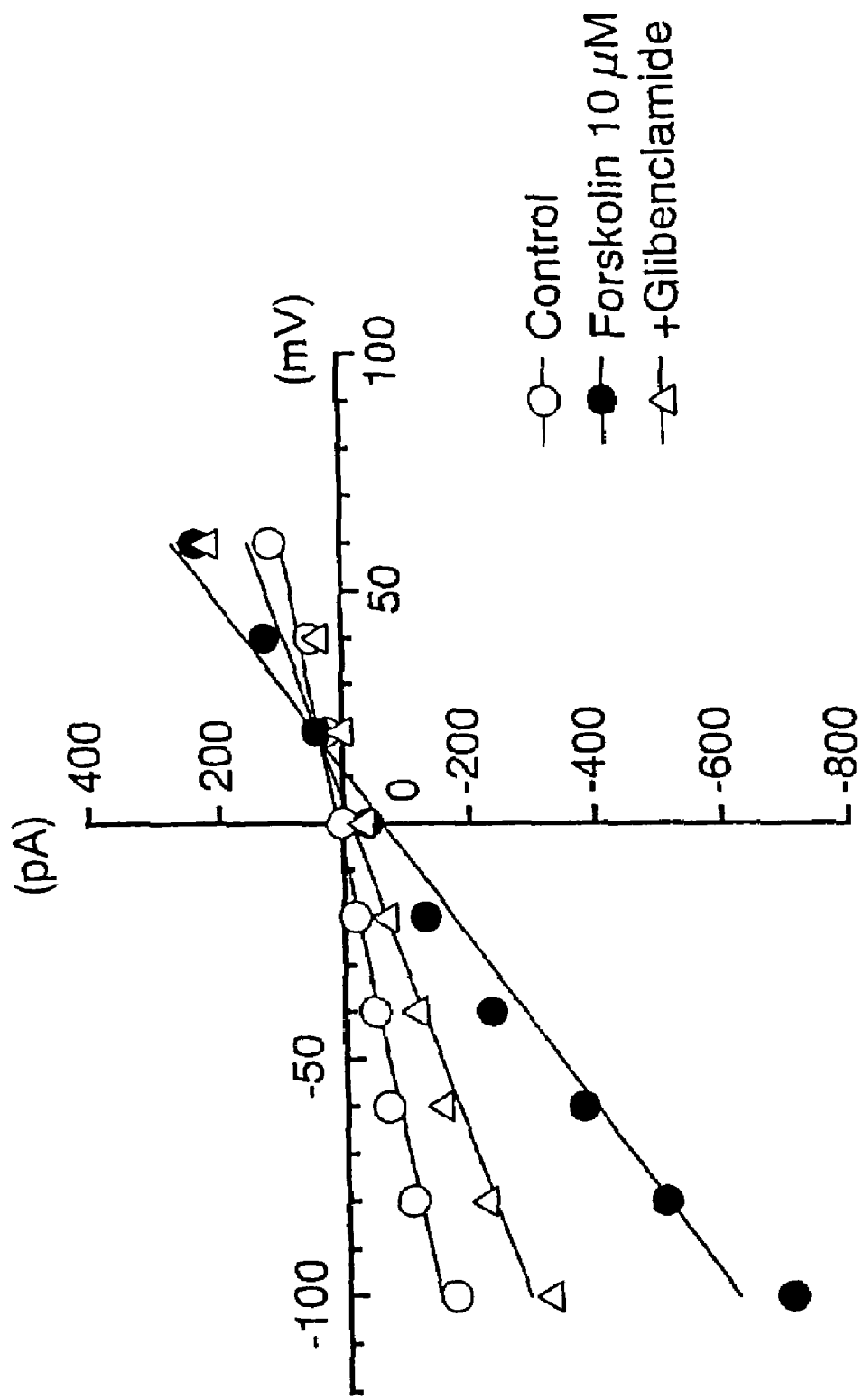
FIG. 16 shows current-voltage relationships obtained in the absence or presence of 10 μM forskolin. The membrane current amplitude was measured as mean value of the last 100 ms of the command pulses (1 s duration). The line was fitted by the least squares method.
Figure 17:
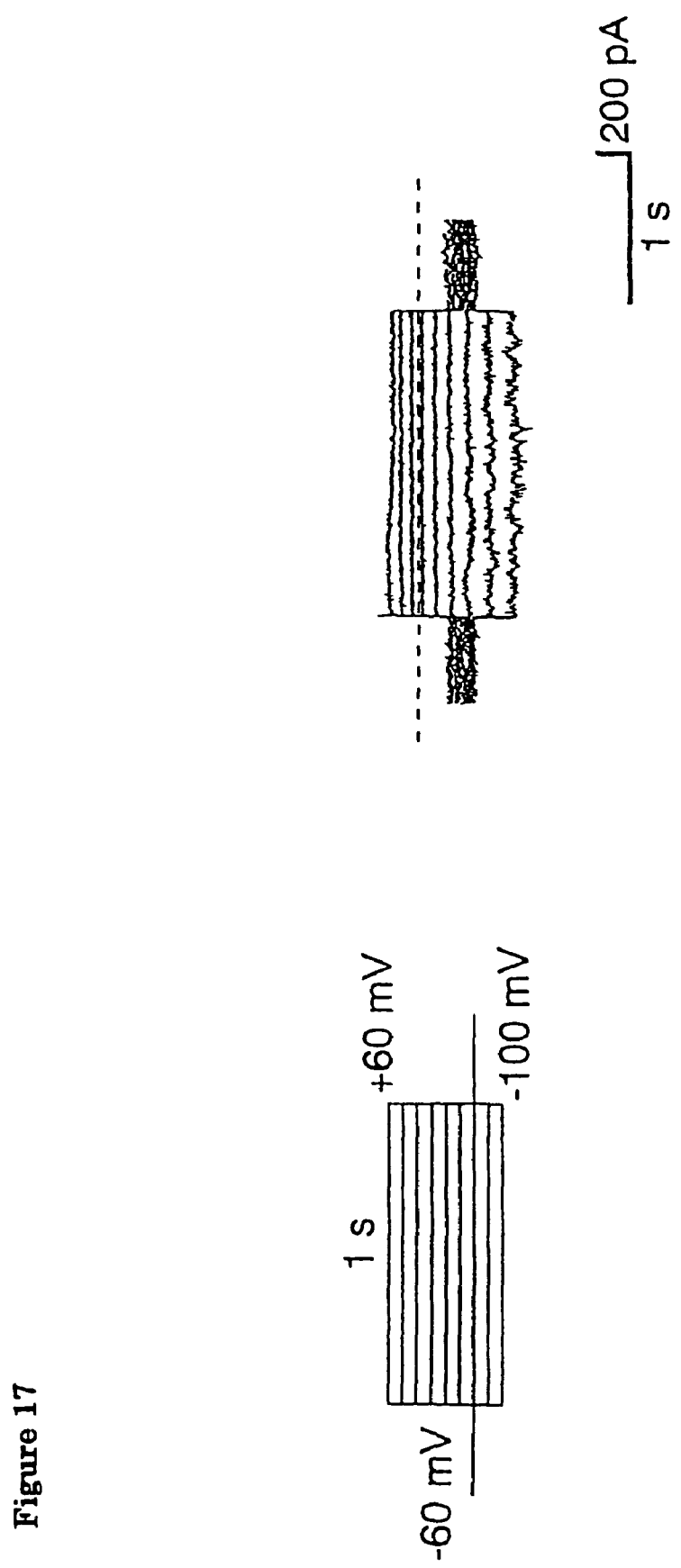
FIG. 17 shows the net membrane current obtained by subtracting the membrane current recorded before the application of forskolin from that recorded during the application of 10 μM forskolin in COS7 cells expressing sample-1 SeV/CFTR. The membrane potential was kept at a holding potential of −60 mV. The dash line indicates the zero current level.

FIG. 16 shows the current-voltage relationships derived based on the above data under the presence or absence of forskolin in COS7 cells expressing sample-1 SeV/CFTR. The lines cross at the point of origin if an endogenous Cl current is not present. In the graph obtained, the lines crossed between 10 and 20 mV. This suggests that a Cl current other than that induced by CFTR (forskolin-independent) is flowing in these COS7 cells. FIG. 17 shows the difference in membrane current in the presence or absence of forskolin (net membrane current) obtained by subtracting the current recorded before the application of forskolin from that recorded during the application of forskolin.

INDUSTRIAL APPLICABILITY

The present invention provides a recombinant Sendai virus vector for introducing exogenous genes to airway epithelia, to which conventional vectors for gene transfer cannot introduce genes efficiently, and a method for introducing exogenous genes using the vector. The recombinant Sendai virus vector of the present invention enables efficient gene transfer to native mucus-layered airway epithelial cells by briefly contacting the vector with the cells. The vector of the present invention can infect airway epithelial cells derived from mammals larger than mice, which suggests that the vector of the present invention enables effective gene therapy in need of gene transfer to airway epithelial cells. Furthermore, the vector of the present invention can introduce genes to not only apical surfaces but also submucosal glands where CFTR primarily expresses, indicating that it can be used for gene therapy of CF, a CFTR-deficient disease.

What is claimed is:

1. A composition comprising a recombinant Sendai virus vector carrying in its genome a cystic fibrosis transmembrane conductance regulator (CFTR) gene, wherein the Sendai virus vector does not contain at least one gene selected from the group consisting of F gene, an HN gene, and an M gene.

2. The composition according to claim 1, wherein the composition further comprises chicken egg chorioallantoic fluid.

3. A method for introducing an exogenous gene into airway epithelia, the method comprising contacting airway epithelia covered with mucus with a composition comprising a recombinant Sendai virus vector carrying an exogenous gene in its genome.

4. A method according to claim 3, wherein the Sendai virus vector does not contain at least one gene selected from the group consisting of an F gene, an HN gene, and an M gene.

5. The method according to claim 4, wherein the composition further comprises chicken egg chorioallantoic fluid.

6. The method according to claim 4, wherein the exogenous gene is a cystic fibrosis transmembrane conductance regulator (CFTR) gene.

7. The method according to claim 3, wherein the composition further comprises chicken egg chorioallantoic fluid.

8. The method according to claim 7, wherein the exogenous gene is a cystic fibrosis transmembrane conductance regulator (CFTR) gene.

9. The method according to claim 3, wherein the exogenous gene is a cystic fibrosis transmembrane conductance regulator (CFTR) gene.

10. The method according to any one of claims 3, 4, 7, 9, 5, 6, or 8, wherein the airway epithelia is present on nose, pharynx, trachea, or any conducting airway or gas-exchange surface in the lung.

11. A method for expressing a cystic fibrosis transmembrane conductance regulator (CFTR) gene in an airway epithelial cell, said method comprising the step of introducing into said cell a recombinant Sendai virus vector carrying in its genome a cystic fibrosis transmembrane conductance regulator (CFTR) gene, wherein said CFTR gene is expressed in said cell.

12. A method according to claim 11, wherein the recombinant Sendai virus vector does not contain at least one gene selected from the group consisting of an F gene, an HN gene, and an M gene.

13. The method according to claim 12, wherein the airway epithelial cell is a nostril epithelial cell, a pharyngeal epithelial cell, a tracheal epithelial cell, or an epithelial cell of a conducting airway or gas-exchange surface in the lung.

14. The method according to claim 11, wherein the airway epithelial cell is a nostril epithelial cell, a pharyngeal epithelial cell, a tracheal epithelial cell, or an epithelial cell of a conducting airway or gas-exchange surface in the lung.

15. A method for expressing an exogenous gene in an airway epithelial cell, said method comprising the step of introducing into said cell a recombinant Sendai virus vector carrying an exogenous gene in its genome, wherein said exogenous gene is expressed in said cell.

16. The method according to claim 15, wherein the recombinant Sendai virus vector does not contain at least one gene selected from the group consisting of an F gene, an HN gene, and an M gene.

17. The method according to claim 15, wherein the exogenous gene is a modified cystic fibrosis transmembrane conductance regulator (CFTR) gene.

* * * * *

SEQUENCE LISTING

```
<160> NUMBER OF SEQ ID NOS: 5

<210> SEQ ID NO 1
<211> LENGTH: 10
<212> TYPE: DNA
<213> ORGANISM: Artificial Sequence
<220> FEATURE:
<223> OTHER INFORMATION: Artificially Synthesized Sequence

<400> SEQUENCE: 1
ctttcaccct                                                           10

<210> SEQ ID NO 2
<211> LENGTH: 15
<212> TYPE: DNA
<213> ORGANISM: Artificial Sequence
<220> FEATURE:
<223> OTHER INFORMATION: Artificially Synthesized Sequence

<400> SEQUENCE: 2
tttttcttac tacgg                                                     15

<210> SEQ ID NO 3
<211> LENGTH: 18
<212> TYPE: DNA
<213> ORGANISM: Artificial Sequence
<220> FEATURE:
<223> OTHER INFORMATION: Artificially Synthesized Sequence

<400> SEQUENCE: 3
cggccgcaga tcttcacg                                                  18

<210> SEQ ID NO 4
<211> LENGTH: 51
<212> TYPE: DNA
<213> ORGANISM: Artificial Sequence
<220> FEATURE:
<223> OTHER INFORMATION: Artificially Synthesized Sequence

<400> SEQUENCE: 4
acttgcggcc gccaaagttc aatgcagagg tcgcctctgg aaaaggccag c              51

<210> SEQ ID NO 5
```

```
<211> LENGTH: 76
<212> TYPE: DNA
<213> ORGANISM: Artificial Sequence
<220> FEATURE:
<223> OTHER INFORMATION: Artificially Synthesized Sequence

<400> SEQUENCE: 5
atccgcggcc gcgatgaact ttcaccctaa gtttttctta ctacggctaa agccttgtat      60
cttgcacctc ttcttc                                                     76
```